(12) United States Patent
Haddad et al.

(10) Patent No.: US 10,464,942 B2
(45) Date of Patent: Nov. 5, 2019

(54) PROCESS FOR THE MANUFACTURE OF IXABEPILONE

(71) Applicant: PHARMAREN, LLC, St. Louis, MO (US)

(72) Inventors: Jalal Haddad, San Diego, CA (US); Sourena Nadji, St. Louis, MO (US)

(73) Assignee: PHARMAREN, LLC, St. Louis, MO (US)

( * ) Notice: Subject to any disclaimer, the term of this patent is extended or adjusted under 35 U.S.C. 154(b) by 0 days.

(21) Appl. No.: 15/817,487

(22) Filed: Nov. 20, 2017

(65) Prior Publication Data

US 2018/0072749 A1    Mar. 15, 2018

Related U.S. Application Data

(63) Continuation-in-part of application No. PCT/US2016/026259, filed on Apr. 6, 2016.

(60) Provisional application No. 62/164,523, filed on May 20, 2015.

(51) Int. Cl.
*A61K 31/427* (2006.01)
*C07D 491/044* (2006.01)
*C07D 493/04* (2006.01)

(52) U.S. Cl.
CPC ........ *C07D 491/044* (2013.01); *A61K 31/427* (2013.01); *C07D 493/04* (2013.01)

(58) Field of Classification Search
CPC .......................... A61K 31/427; C07D 417/06
USPC ................................ 514/365; 548/181, 204
See application file for complete search history.

(56) References Cited

U.S. PATENT DOCUMENTS 6,365,749 B1    4/2002  Kim et al.
2005/0038086 A1  2/2005  Ashley et al.

OTHER PUBLICATIONS

Su, et al., Total Synthesis of (−) Epothilone B; An Extension of Suzuki Coupling Method and Insights Into Structure-Activity Relationships of the Epothilones, Agnew Chem Int. Ed., 1998, 36:7:757-759.
Balog, et al., A novel Aldol Condensation with 2-Methyl-4-pentenal and Its Application to An Improved Total Synthesis of Epothilone B, Angew Chem Int. Ed. 1998, 37:19:2675-3678.
Schinzer, et al., Syntheses of (−)Epothilone B, Chem Eur J, 1999, 5:9:2492-2500.
International Search Report issued in PCT/US2016/26259 dated Jul. 26, 2016.
Biswas, et al., Highly Concise Routes to Epothilones: The Total Synthesis and Evaluation of Epothilone 490, J. Am. Chem. Soc., 2002, 124:9825-9832.
Lee, et al., Insights into Long-Range Structural Effects on the Stereochemistry of Aldol Condensations: A Practical Total Synthesis of Desoxyepothilone F, J. Am. Chem. Soc., 2001, 123:5249-5259.
Mulzer, et al., Total Syntheses of Epothilones B and D, J. Org. Chem., 2000, 65:7456-7467.
Nicolaou, et al., Total Syntheses of Epothilones A and B via a Macrolactonization-Based Strategy, J. Am. Chem. Soc., 1997, 119:7974-7991.
Prantz, et al., Decarboxylative Grob-Type Fragmentations in the Synthesis of Trisubstituted Z Olefins: Application to Peloruside A, Discodermolide and Epothilone D**, Angrew. Chem. Int. Ed., 2009, 48:5030-5033.
Rivkin, et al., Complex Target-Oriented Total Synthesis in the Drug Discovery Process: The Discovery of a Highly Promising Family of Second Generation Epothilones, J. Am. Chem. Soc., 2003, 125:2899-2901.
Stachel, et al., On the Interactivity of Complex Synthesis and Tumor Pharmacology in the Drug Discovery Process: Total Synthesis and Comparative in Vivo Evaluations of the 15-Aza Epothilones, J. Org. Chem., 2001, 66:4369-4378.
Valluri, et al., Total Synthesis of Epothilone B, Organic Letters, 2011, 3:23:3607-3609.
White, et al., Tottal Synthesis of Epothilone B, Epothilone D, and cis- and trans-9,10-Dehydroepothilone D, J. Am. Chm. Soc., 2001, 123:5407-5413.
Zhan, et al., Design and Synthesis of C6-C8 Bridged Epothilone A., Organic Letters, 2008, 10:8:1565-1568.
Zhu, et al., Total Synthesis of Epothilone A, Organic Letters, 2000, 2:17:2575-2578.

*Primary Examiner* — Jeffrey H Murray
(74) *Attorney, Agent, or Firm* — Blank Rome LLP

(57) ABSTRACT

The invention relates to the process of manufacturing Epothilone compounds of Formulas I-IV. The process of the present invention is totally synthetic, utilizes highly pure and crystalline Epothilone B, and produces ixabepilone in high efficiency, purity, and yield.

30 Claims, 10 Drawing Sheets

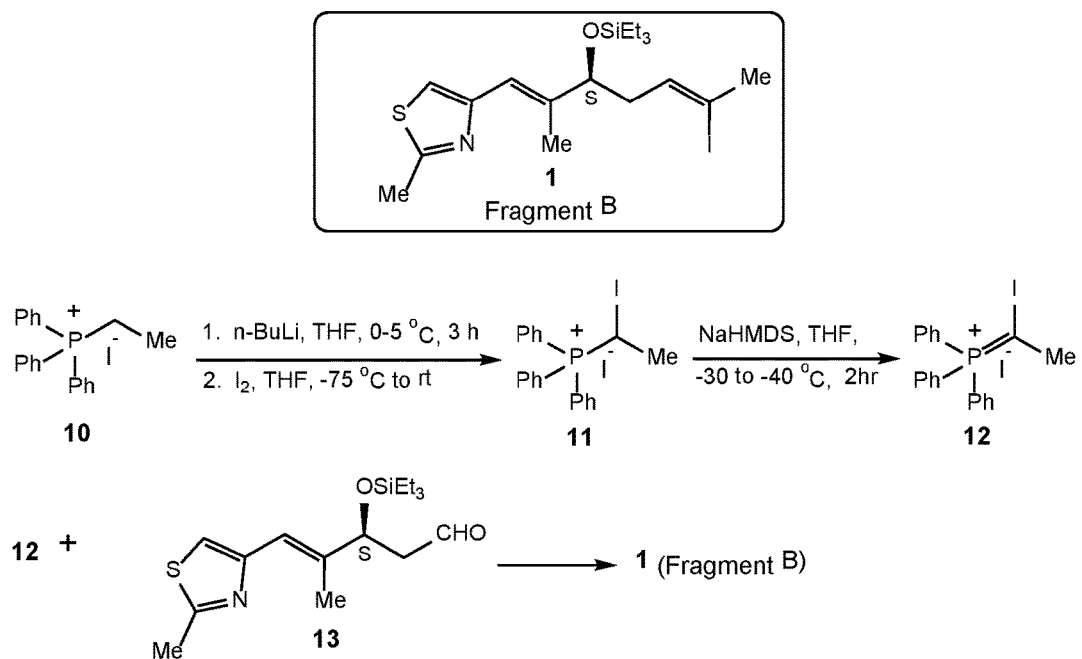
Fig. 1. Synthesis of Fragment B (1).

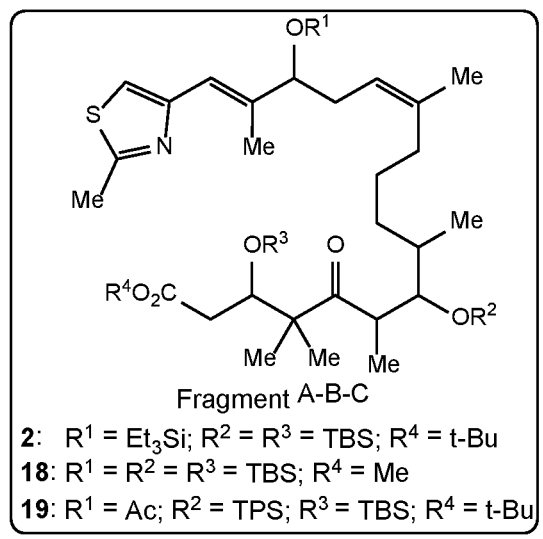

Fragment A-B-C
2: $R^1 = Et_3Si$; $R^2 = R^3 = TBS$; $R^4 = t\text{-}Bu$
18: $R^1 = R^2 = R^3 = TBS$; $R^4 = Me$
19: $R^1 = Ac$; $R^2 = TPS$; $R^3 = TBS$; $R^4 = t\text{-}Bu$

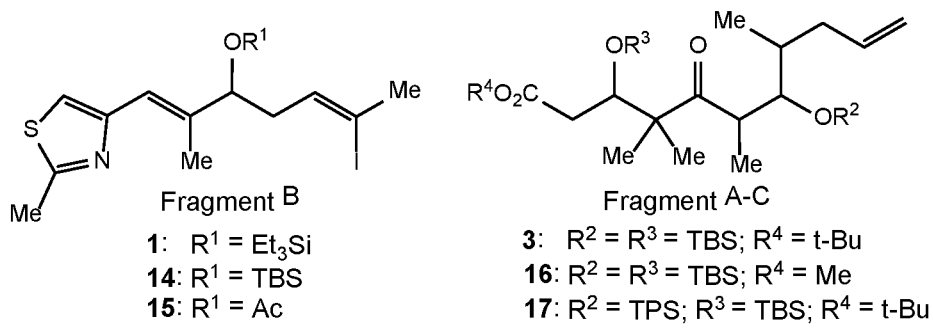

Fragment B
1: $R^1 = Et_3Si$
14: $R^1 = TBS$
15: $R^1 = Ac$

Fragment A-C
3: $R^2 = R^3 = TBS$; $R^4 = t\text{-}Bu$
16: $R^2 = R^3 = TBS$; $R^4 = Me$
17: $R^2 = TPS$; $R^3 = TBS$; $R^4 = t\text{-}Bu$ Present Invention

Broarup et al., and Avery et al.

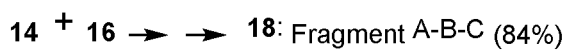

Danishefsky et al.

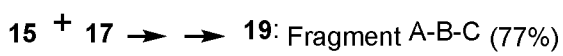

Fig. 2. Synthesis of Fragment A-B-C (2): Prior Art and Present Invention.

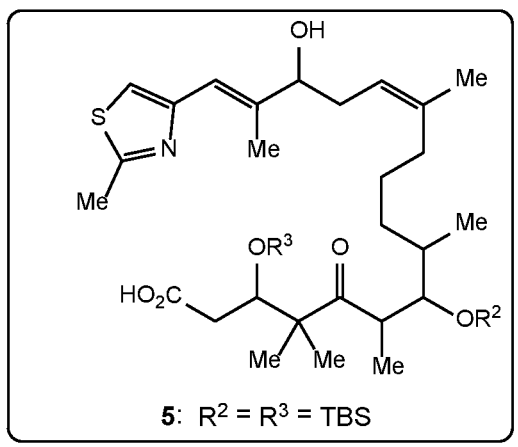
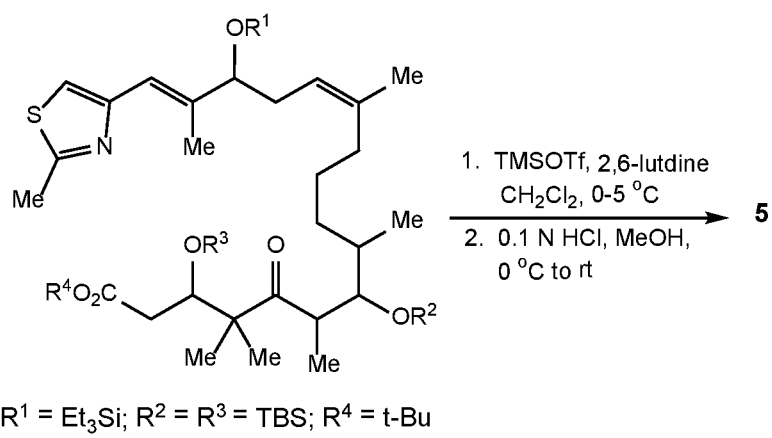
Fig. 3. Deprotection of Fragment A-B-C.

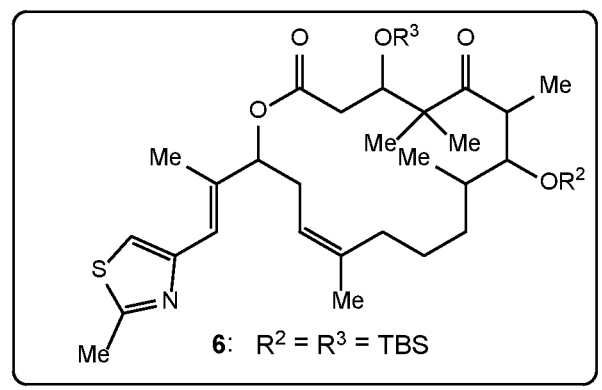
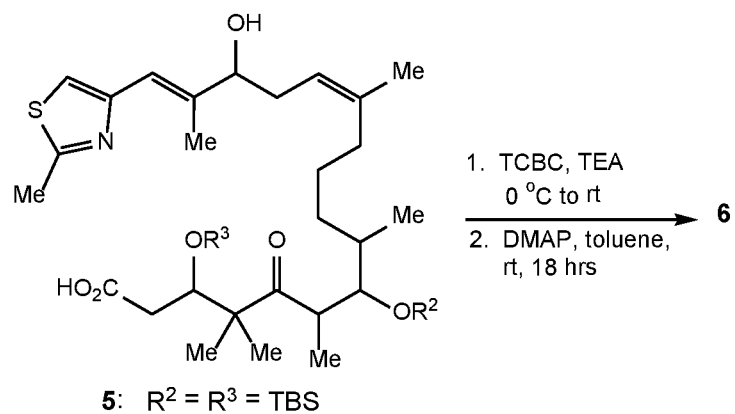
Fig. 4. Macrolactonization of Deprotected Fragment A-B-C.

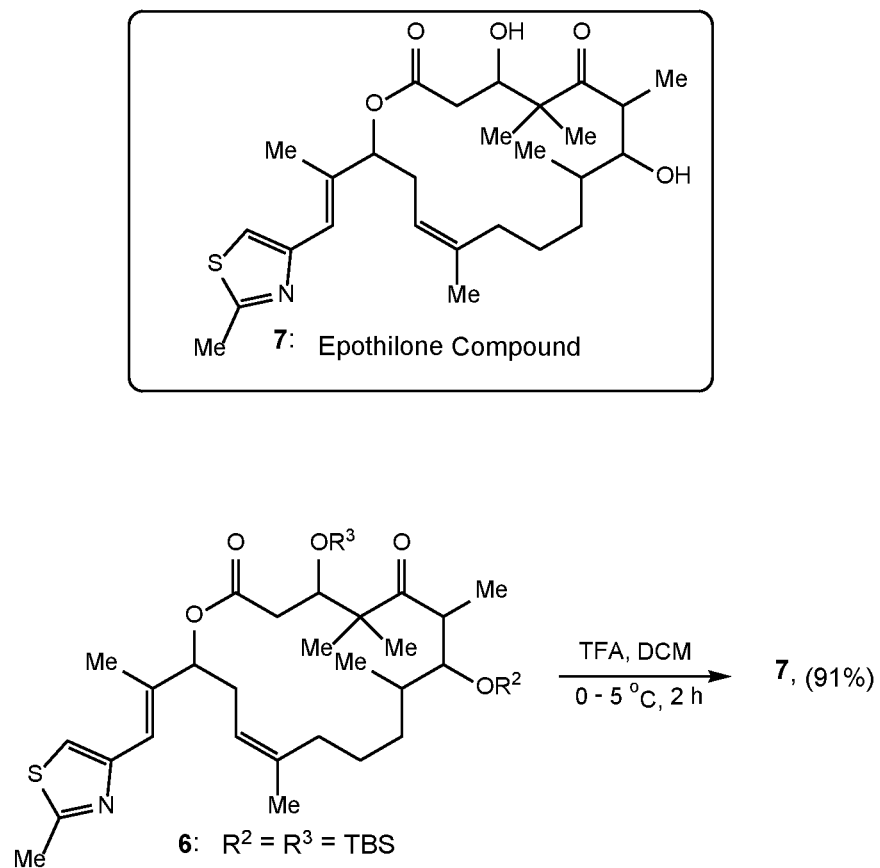
Fig. 5. Synthesis of Epothilone Compound 7.

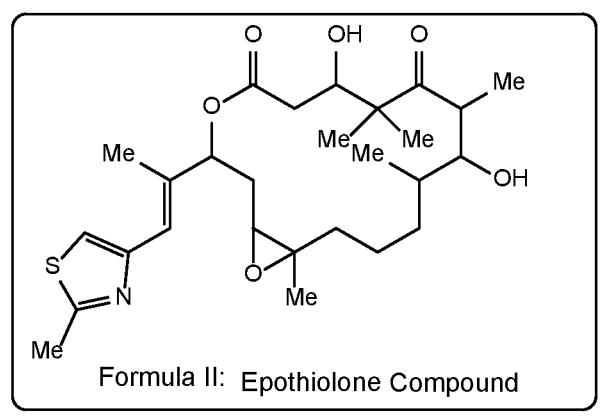
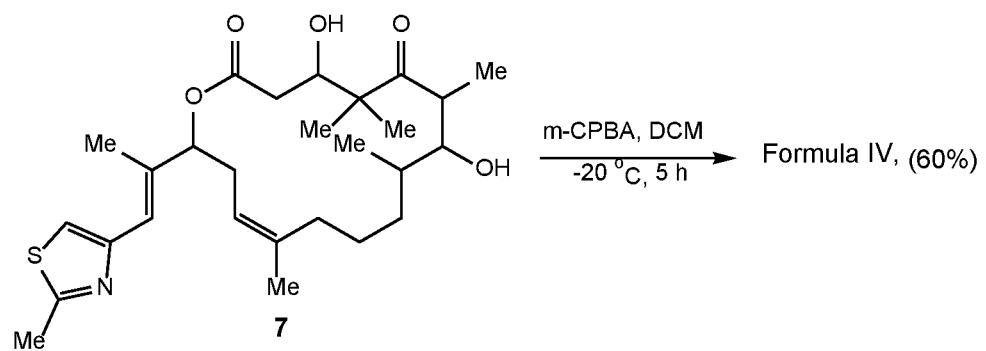
Fig. 6. Synthesis of Epothilone Compound of Formula II.

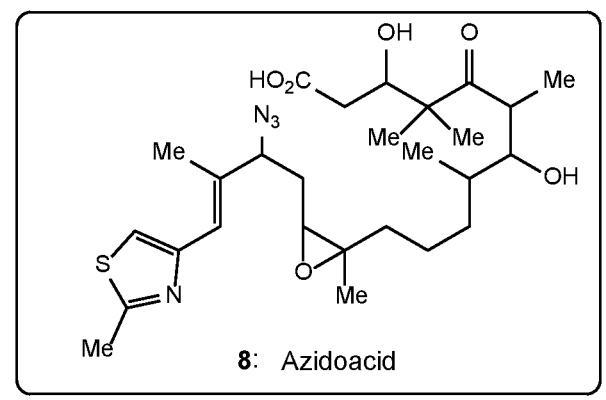
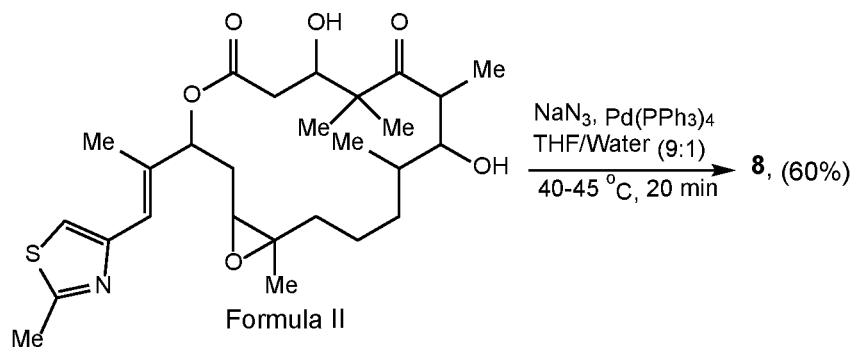
Fig. 7. Synthesis of Azidoacid 8.

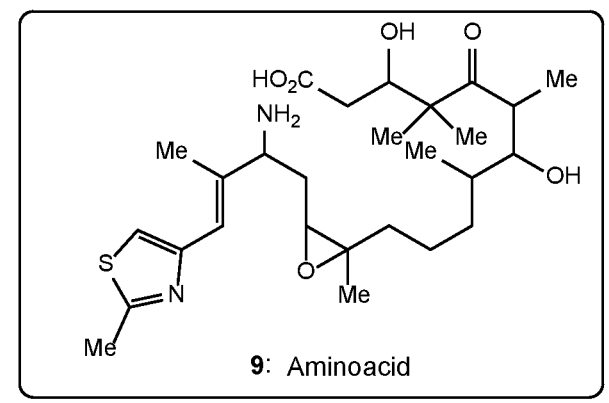
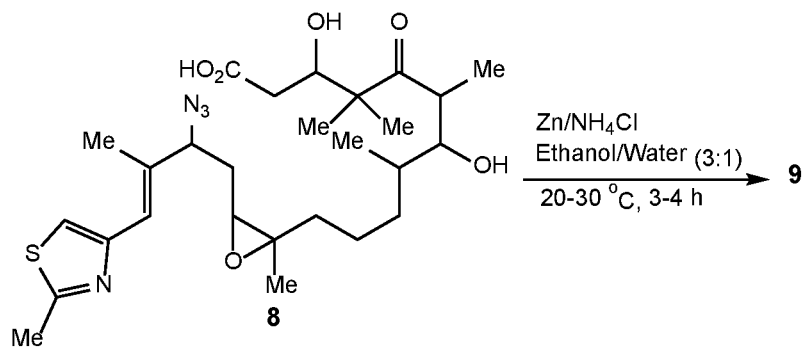
Fig. 8. Synthesis of the Aminoacid 9.

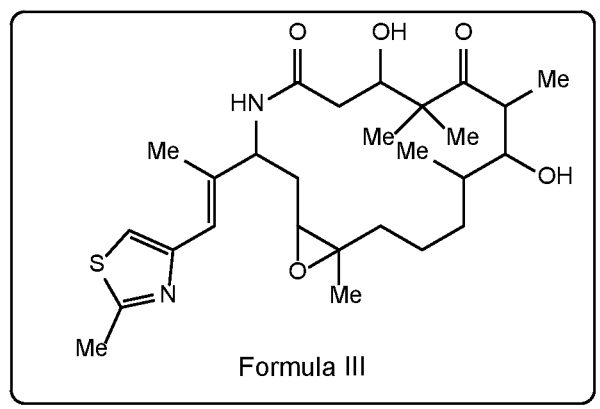
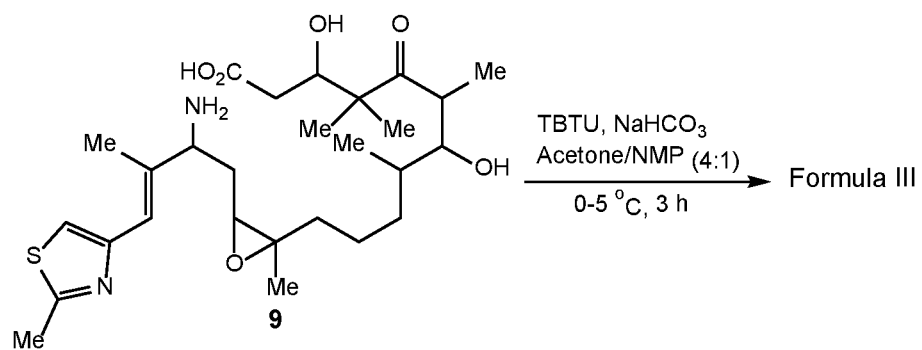
Fig. 9. Synthesis of Epothilone Compound of Formula III.

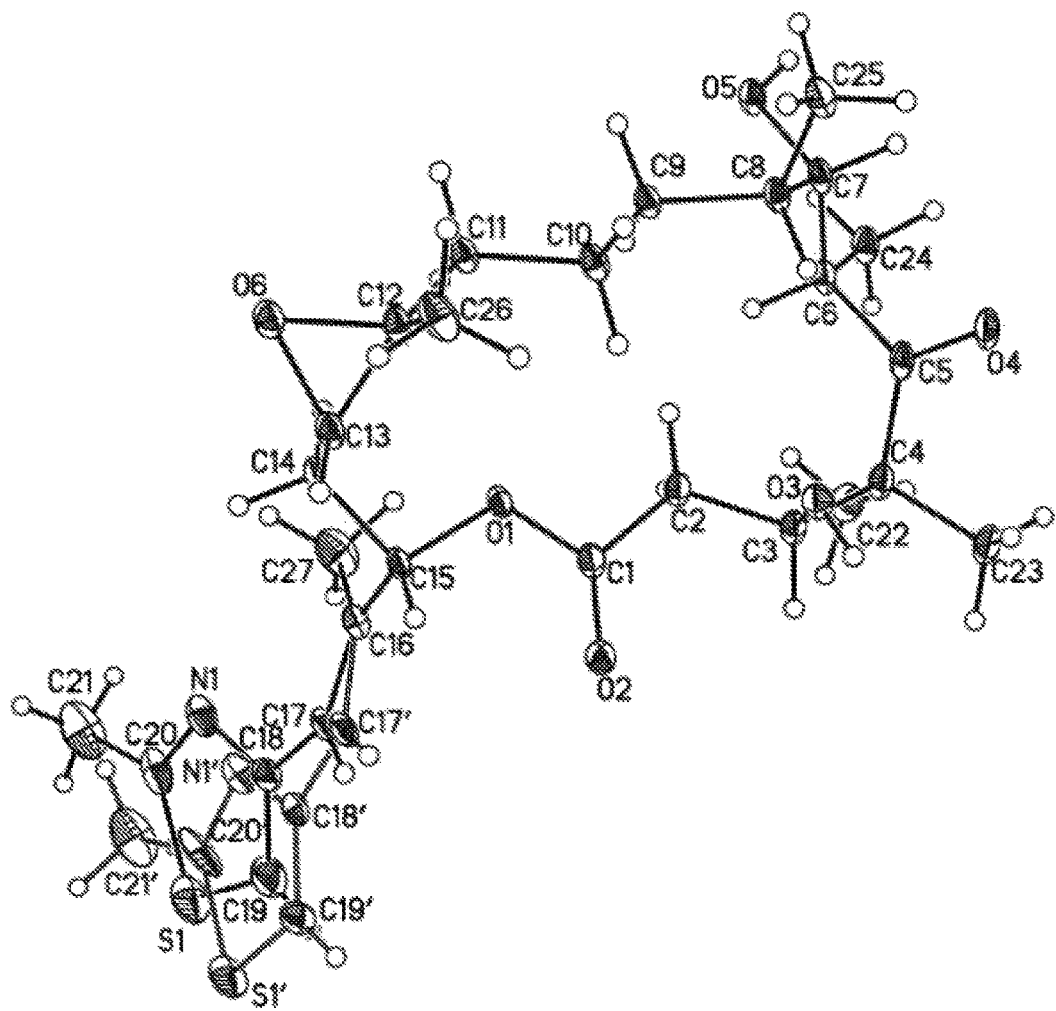
Fig. 10. X-Ray Crystal Structure of Epothilone B.

PROCESS FOR THE MANUFACTURE OF IXABEPILONE

This application is a continuation-in-part of International Patent Application No. PCT/US2016/026259, filed Apr. 6, 2016, which claims the benefit of U.S. Provisional Application No. 62/164,523 filed May 20, 2015, both of which are hereby incorporated by reference.

FIELD OF THE INVENTION

This invention relates to the synthetic process for manufacturing the antitumor agent, Ixabepilone via the key intermediate, Epothilone B.

PRELIMINARY NOTE

Various prior art references in the specification are indicated by italicized Arabic numerals in brackets. Full citation corresponding to each reference number is listed at the end of the specification, and is herein incorporated by reference in its entirety in order to describe fully and clearly the state of the art to which this invention pertains. Unless otherwise specified, all technical terms and phrases used herein have their art-recognized meaning, which can be found by reference to standard texts, journal references, and contexts known to those skilled in the art as established by International Union of Pure and Applied Chemistry (IUPAC), the American Chemical Society (ACS), and other international professional societies. The rules of nomenclature are described in various publications, including, "Nomenclature of Organic Compounds,"[1] and "Systematic Nomenclature of Organic Chemistry"[2], which are herein incorporated by reference in their entireties.

BACKGROUND

Epothilones are a class of macrocyclic lactones that were originally isolated from myxobacterium *Sorangium Cellulosum*[3]. They are potent antitumor agents whose activity is akin to that of taxol derivatives, but with better efficacy and milder side effects. Like Taxols, Epothilones elicit antitumor effect by inhibiting microtubule function thereby preventing mitosis (cell division). To date, six Epothilone ('Epo') derivatives (Epo A-F) have been identified, and all of them possess the macrocyclic 16-membered ring lactone core. Due to their remarkable antitumor property, Epothilones have attracted considerable attention, and hundreds of articles related to the structure, synthesis, and biological activities of both natural and synthetic Epothilones have been published. Danishefsky et al. reported the first total synthesis of Epo A in 1996 and of Epo B-F subsequently.[4] Since then, many other groups have attempted to develop efficient and commercially viable synthetic methods for both the natural products as well the synthetic analogs. Several synthetic analogs are undergoing clinical trials, and one of the analogs, Ixabepilone (I) (the active pharmaceutical ingredient (API) in IXEMPRA™) displays greater metabolic stability than its precursor, and has been approved by FDA for the treatment of metastatic breast cancer. Ixabepilone ('Ixa') is the lactam analog of Epo B (II), and is currently being synthesized from II. The total synthesis of Epo B (2), which is the key intermediate in the synthesis of Ixa, was achieved earlier by Danishefsky et al.,[5] and more recently by Wang et al.[6] The conversion of Epo B to Ixabepilone has been reported by Kim et al.,[7] which is hereby incorporated by reference in its entirety.

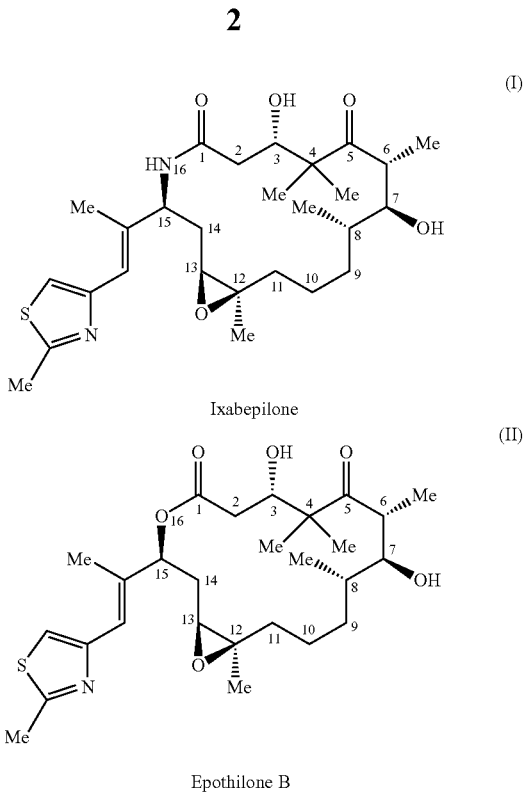

Ixabepilone

Epothilone B

All the prior art methods for the production of Epo B and Ixa fall into two general approaches: fermentation and total synthesis. Both are best with two major problems. The major problem with the fermentation approach is the lack of control of the biosynthesis of Epo B, which results in the formation of a complex mixture of products that warrants an elaborate and tedious process for the isolation and purification of II. This, in turn, has a considerable impact on the overall yield. On the other hand, the total synthesis approach has consistently been suffering from poor scalability and yields. Nevertheless, the synthetic approach offers important advantages over the fermentation process in that the former offers a potentially better "scalability" prospect and superior control over side reactions, which both are important factors in having a reproducible process and reliable impurity profiles at each step. Accordingly, the objective of the present invention is to develop an efficient, practical, and totally synthetic process of Epo B (I) and transform it to its lactam analog, Ixa (II), at a manufacturing scale.

SUMMARY

The present inventions relates to the process of manufacturing Epo B (II), the key intermediate, and Ixa (I), the final product. The process involves several stages as described in FIGS. 1-10: (1) Synthesis of Fragment B; (2) Synthesis of Fragment A-B-C; (3) Deprotection of Fragment A-B-C; (4) Macrolactonization of Fragment A-B-C; (5) Synthesis of Epothilone D; (6) Synthesis and Crystallization of Epothilone B (II); (7) Synthesis of the Azide intermediate; (8) Synthesis of the Amino Acid intermediate; and (9) Synthesis and crystallization of the final compound, Ixabepilone (I). Unlike the methods described in the prior art publications, the present invention describes a process that is totally synthetic and utilizes highly pure and crystalline Epothilone B. The process also produces Ixabepilone in higher efficiency, purity, and yield compared to the fermentation or semi-synthetic route.

BRIEF DESCRIPTION OF THE DRAWINGS
FIG. 1. Synthesis of Fragment B (1).
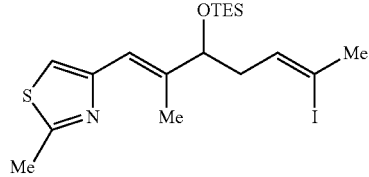
FIG. 2. Synthesis of Fragment A-B-C (2).
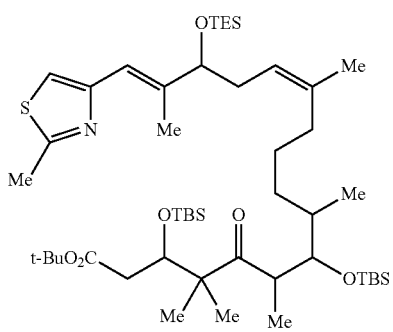
FIG. 3. Deprotection of Fragment A-B-C (5).
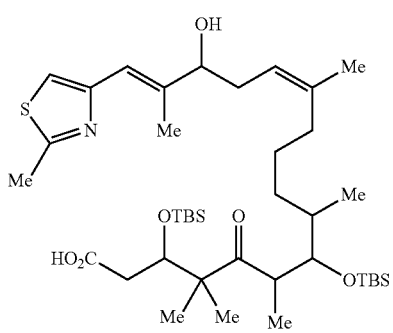
FIG. 4. Macrolactonization of Deprotected Fragment A-B-C (6).
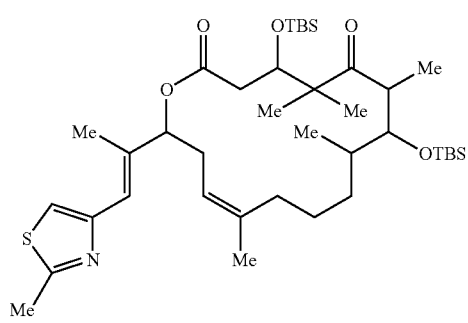
FIG. 5. Synthesis of Epothilone Compound (7).
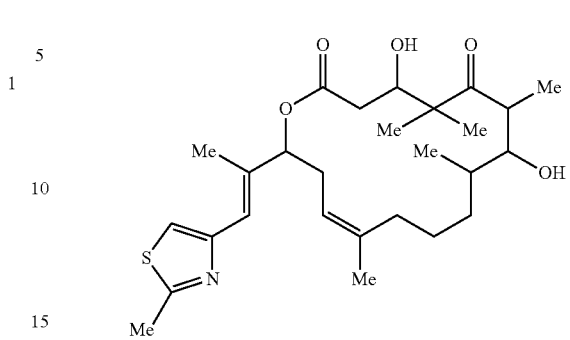
FIG. 6. Synthesis of Epothilone Compound of Formula (IV).
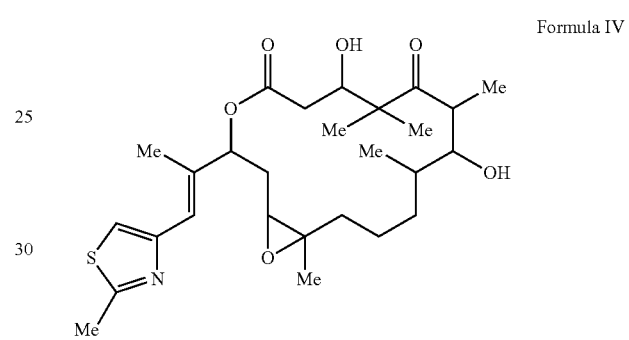
FIG. 7. Synthesis of the Azidoacid (8).
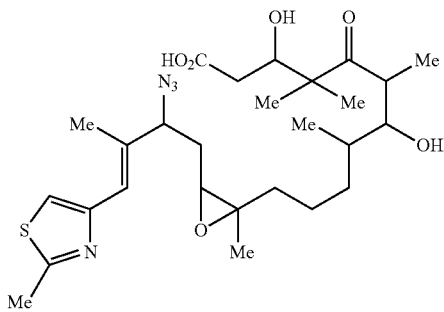
FIG. 8. Synthesis of the Aminoacid (9).
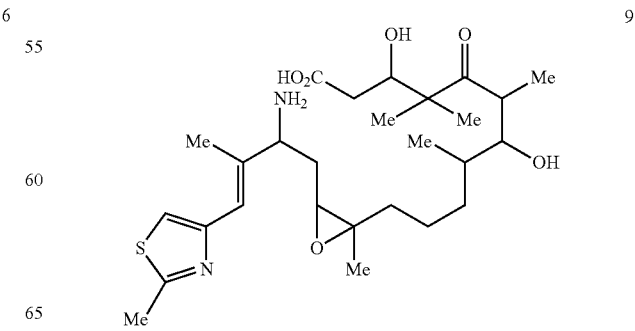

FIG. 9. Synthesis of Epthilone Compound of Formula III.

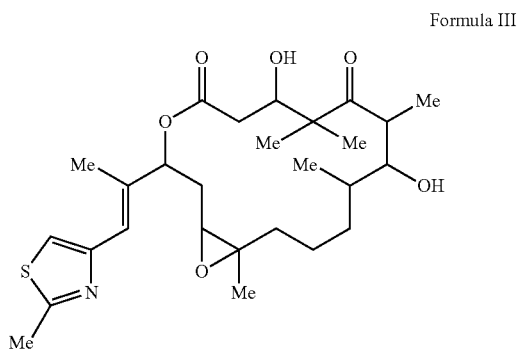 [SMILES: C/C(=C\c1csc(C)n1)C1CC2OC2(C)CCCC(C)C(O)C(C)C(=O)C(C)(C)C(O)CC(=O)O1]

Formula III

FIG. 10. X-Ray Crystal Structure of Epothilone B.

DETAILED DESCRIPTION

The total synthesis of Ixabepilone involves nine stages. A representative procedure for the preparation of about 10 grams of Epothilone B and about 1 gram of Ixabepilone is provided in detail below, but the batch size may be increased or decreased as needed. It is further emphasized that the temperature ranges, weight and volumes for the reagents and solvents, and the reaction times are exemplary for said batch size, and should not be construed as being limiting. These parameters may be varied depending on the batch size desired. It is well understood in the art that minor deviations (ca. <20%) from the specified procedure do occur occasionally and are permissible within the scope of the invention. The methods of the present invention are detailed in the following procedures which are offered by way of illustration and are not intended to limit the scope of the invention in any manner.

The first stage of the process is the synthesis of Fragment B (1) in two steps from the known starting material 13.[8] Two separate procedures (with or without isolation of compound 2) are described below.

METHOD A. Via Isolation of Compound 2.

Step 1.1

| Reagent | MW | Amount | mmol | Equiv. |
|---|---|---|---|---|
| 10 | 418.26 | 100 g | 239 | 1 |
| n-BuLi, 2.5M in Hexanes | | 95 mL | 237 | 0.98 |
| Anhydrous THF | | 550 mL | | 5.5 vol. |

Purge a 2-L, three-neck, RBF equipped with a mechanical stirrer, a J-Kem temperature controller, and a nitrogen inlet with nitrogen.

Charge the flask with 10 and THF. Cool the batch to about −5-10° C., preferably 0-5° C.

Add n-BuLi to the suspension of 10 in THF at −5-10° C., preferably 0-5° C., drop-wise over about 50 min. A minor excursion above or below this temperature range is permissible, and may not adversely affect the reaction.

Allow the resulting red solution stir at the same temperature for 2 h.

Step 1.2

| Reagent | MW | Amount | mmol | Equiv. |
|---|---|---|---|---|
| Iodine | 254 | 57.7 g | 227 | 0.95 |
| Anhydrous THF | | 865 mL | | 15 vol. |

Purge a 3-L, three-neck, RBF equipped with a mechanical stirrer, a J-Kem temperature controller, and a nitrogen inlet with nitrogen.

Charge the flask with iodine and THF.

Cool the batch to about −75±10° C. A minor excursion above or below this temperature range may not adversely affect the reaction.

Transfer the ylide solution prepared above into the iodine solution at about −72±10° C., preferably at −72±2° C., over 55 min. A minor excursion above or below this temperature range may not adversely affect the reaction.

Allow the resulting beige suspension agitate and warm to about 10° C. over about 3 h. A minor excursion above or below this temperature range may not adversely affect the reaction.

Dilute the suspension with hexanes (about 400±40 mL).

Filter the solid under a blanket of nitrogen and wash the cake with hexanes (about 2×200 mL).

Dry the solid under HIVAC at about 30-35° C. for about 18 hours, preferably 18-24 h.

Using the procedure described in Steps 1.1 and 1.2, the intermediate 11 was obtained as light beige solid, 126.5 g (97% yield). NMR consistent with the structure.

Step 2.1

| Reagent | MW | Amount | mmol | Equiv. |
|---|---|---|---|---|
| 2 | 544.2 | 126.5 g | 232 | 2.5 |
| NaHMDS, 1.0M in THF | | 232 mL | 232 | 2.5 |
| Anhydrous THF | | 1250 mL | | 10 vol. |

Purge a 3-L, three-neck, RBF equipped with a mechanical stirrer, a J-Kem temperature controller, and a nitrogen inlet with nitrogen.

Charge the flask with compound 11 and THF.

Cool the batch to about −35° C.

Add sodium hexamethyldisilazide (NaHMDS) drop-wise to the suspension of 11 in THF at about −35±10° C., preferably at −35±5° C. over about 30 min.

Allow the resulting brown-red solution stir at the same temperature for 30 min.

Step 2.2

| Reagent | MW | Amount | mmol | Equiv. |
|---|---|---|---|---|
| Aldehyde 3 | 325.5 | 30.2 | 92.8 | 1 |
| Anhydrous THF | | 300 ml | | 10 vol. |

Prepare a solution of aldehyde 13 in THF under nitrogen.

Add the solution of 13 to the ylide solution prepared above at about −40±10° C., preferably at −40±5° C. over about 95 min.

Allow the solution to stir at the same temperature for 3 h.

Quench the solution with a saturated solution of NH$_4$Cl (60 mL) at about −40±15° C., preferably at −40±5° C. over about 5 min.

Allow the resulting beige suspension to agitate and warm to about 0° C. over about 1 h.

Dilute the batch with hexanes (600 mL) and allow to warm to about 5-20° C., preferably to about 10-15° C.
Filter the batch through a short pad of Celite and wash the cake with 10% EtOAc in hexanes or heptanes (about 2×250 mL).
Concentrate the filtrate to a light brown oil (~81 g).
Purify on silica gel eluting with 0-2% EtOAc in hexanes or heptanes.
Concentrate and dry under HIVAC at 25-30° C. for about 18-24 h.
Using the procedure in Steps 2.1 and 2.2 above, Fragment B (1) was obtained as a colorless oil, 24.02 g (55.8% yield). NMR consistent with the structure.

METHOD B: One-Pot Reaction
Step 3.1

| Reagent | MW | Amount | mmol | Equiv. |
|---|---|---|---|---|
| 1 | 418.26 | 100 g | 239 | 1 |
| n-BuLi, 2.5M in Hexanes | | 95 mL | 237 | 0.98 |
| Anhydrous THF | | 550 mL | | 5.5 vol. |

Purge a 2-L, three-neck, RBF equipped with a mechanical stirrer, a J-Kem temperature controller, and a nitrogen inlet with nitrogen. Charge the flask with 1 and THF. Cool the batch to −5-10° C., but preferably at 0-5° C.
Add n-BuLi drop-wise to the suspension of 1 in THF at about −5-10° C., but preferably at 0-5° C. over 50 min.
Allow the resulting red solution stir at the same temperature for about 2 h.
Step 3.2

| Reagent | MW | Amount | mmol | Equiv. |
|---|---|---|---|---|
| Iodine | 254 | 57.7 g | 227 | 0.95 |
| Anhydrous THF | | 865 mL | | 15 vol. |

Purge a 3-L, three-neck, RBF equipped with a mechanical stirrer, a J-Kem temperature controller, and a nitrogen inlet with nitrogen.
Charge the flask with iodine and THF.
Cool the batch to about −75° C.
Transfer the ylide solution prepared above into the iodine solution at about −75±10° C., but preferably at −72±2° C. over 55 min.
Allow the resulting beige suspension agitate and warm to ambient temperature (15-25° C.), preferably at 22±2° C. over few hours.
Use the suspension for the next step within 15-20 h.
Step 3.3

| Reagent | MW | Amount | mmol | Equiv. |
|---|---|---|---|---|
| 11 | 544.2 | 126.5 g | 232 | 2.5 |
| NaHMDS, 1.0M in THF | | 232 mL | 232 | 2.5 |
| Anhydrous THF | | 1250 mL | | 10 vol. |

Cool the suspension prepared above to about −35° C.
Add NaHMDS drop-wise to the suspension of 11 in THF at −35±10° C., but preferably at −35±5° C. over about 30 min.
Allow the resulting brown-red solution stir at the same temperature for about 30 min.

Step 3.4

| Reagent | MW | Amount | mmol | Equiv. |
|---|---|---|---|---|
| Aldehyde 13 | 325.5 | 30.2 | 92.8 | 1 |
| Anhydrous THF | | 300 mL | | 10 vol. |

Prepare a solution of aldehyde 13 in THF under nitrogen.
Add the solution of 13 to the ylide prepared above at −40±10° C., but preferably at −40±5° C. over about 95 min.
Allow the solution to stir at the same temperature for about 3 h.
Quench the solution with a saturated solution of NH$_4$Cl (60 mL) at −40±10° C., but preferably at −40±5° C. for about 5 min.
Allow the resulting beige suspension to agitate and warm to about 0° C. over about 1 h.
Dilute the batch with hexanes (600 mL) and allow to warm to about 5-20° C., but preferably at 10-15° C.
Filter the batch through a short pad of Celite and wash the cake with 10% EtOAc in hexanes or heptanes (2×250 mL).
Concentrate the filtrate to a light brown oil (~80 g).
Purify on silica gel eluting with 0-2% EtOAc in hexanes or heptanes.
Concentrate and dry under HIVAC at 25-30° C. for about 18-24 h.
Using the procedure described in Steps 3.1 to 3.4, Fragment B (1) was obtained as a colorless oil, 21.7 g (50.4% yield). NMR was consistent with the structure of the compound.

The second stage of the process is the synthesis of Fragment A-B-C (2) in two steps starting with Fragment B and Fragment A-C. The coupling of these two fragments (or similar derivatives thereof) to give the C12-C13 alkene derivates 2, 18, or 19 (or similar derivative thereof) is the key step in the synthesis of all Epo B derivatives not only in the process of the present invention, but in all others disclosed previously.[8] Such a condensation reaction joining said two Fragments have been previously achieved by Suzuki[5-6], Wittig[9], or olefin metathesis reactions.[6,10] All of these reactions produce a mixture of E and Z trisubstituted isomers, but the Z isomer is preferred. It should be emphasized that the overall yield and the Z/E ratio of the condensed product specially in the Suzuki coupling route are very sensitive to the nature of the substituents in their respective fragments, $R^1$, $R^2$, and $R^3$, and, hence, are unpredictable [cf. Table 1]. Danishefsky et al.[8,11] have published several methods for the synthesis of fragment ABC using Suzuki coupling reaction with the yields ranging from 50-77% (FIG. 2). It should be noted that in the case of the reaction that produced highest yield (i.e., 77%), the coupled product was in different oxidation states which required an additional oxidation step. Broadrup et al.[12] and Avery et al.[13] (FIG. 2) have independently reported yields of 84% and 85% respectively in Suzuki coupling step. However, in their synthesis, the carboxyl group was protected as the methyl ester, and neither of them reported on the condition and the yield of the saponification of the ester. Therefore, as the ester hydrolysis is a crucial step for the next stage of the reaction, viz., the Yamagushi macrolactonization to give the fully-protected Epo D, we had directed considerable efforts in developing an optimal method for the deporotection of the methyl ester. Unfortunately, we observed that any condition employed for the saponification of the methyl ester resulted in substantial loss of t-butyldimethylsilyl (TBS) protecting group ($R^3$) as well. However, in our process, the use of t-butyl protecting group for the carboxyl functionality resolved this problem.

During the course of our investigation, we discovered that the nature of the hydroxyl protecting groups $R^1$, $R^2$ and $R^3$ strongly influences the yield of the Suzuki coupling reaction, albeit the precise mechanism is not yet understood. Hence, our modified Suzuki process, which is described in detail below, incorporates the most appropriate protecting groups in the two fragments resulting in a high isolated yield of the product (ca. 95%). Comparative yields of the product from the present invention and from the prior art processes are given in Table 1.

TABLE 1

Suzuki Coupling Reaction

| Laboratory | $R^1$ | $R^2$ | $R^3$ | $R^4$ | Yield | Ref. |
|---|---|---|---|---|---|---|
| Present Invention | SiEt$_3$ | TBS | TBS | COO t-Bu | 95% | |
| Broarup et al. | TBS | TBS | TBS | COOMe | 84% | 12 |
| Danishefsky et al. | Ac | TPS | TBS | CH(OMe)$_2$ | 77% | 11b |
| Danishefsky et al. | SiEt$_3$ | SiEt$_3$ | Troc | COO t-Bu | 72% | 11a |
| Danishefsky et al. | Ac | TBS | TBS | COO TBS | 56% | 11c |
| Danishefsky et al. | TBS | O | Troc | COO t-Bu | 60% | 11c |
| Shibasaki et al. | TBS | TBS | TBS | COOPh | 50% | 14 |
| Panek et al. | Ac | TBS | Bn | COO TBS | 60% | 15 |
| Wong et al. | Ac | TBS | PMB | COO t-Bu | 65% | 16 |
| Avery et al. | TBS | TBS | TBS | COOMe | 84% | 13 |

Ac = acetyl;
Bn = benzyl;
TBS = t=butyldimethylsilyl;
TPS = Triphenylsilyl;
Troc = 2,2,2-trichloroethyl carbonate Step 4.1

| Reagent | MW | Amount | mmol | Equiv. |
|---|---|---|---|---|
| Fragment A-C (3) | 556.97 | 53.6 g | 96.2 | 1.3 |
| 9-BBN-H, 0.5M in THF | | 217 mL | 108.3 | 1.5 |
| Anhydrous THF | | 65 mL | | 1.2 vol. |

Purge a 500-mL, three-neck, RBF equipped with a mechanical stirrer, a J-Kem temperature controller, and a nitrogen inlet with nitrogen.
Charge the flask with 3 and THF.
Add 9-BBN-H via an addition funnel at about 20±10° C., but preferably at 22±4° C. drop-wise over 5 min. Allow the solution stir at the same temperature for about 1 h.
Quench the excess of 9-BBN with DI water (31 mL) at about 20±10° C., but preferably at 23±3° C. over 5 min. Allow the mixture stir at the same temperature for 10 min.

Step 4.2

| Reagent | MW | Amount | mmol | Equiv. |
|---|---|---|---|---|
| Fragment B (1) | 463.49 | 33.5 g | 72.2 | 1 |
| Pd(dpf)Cl$_2$ | 816.64 | 5.9 g | 7.22 | 0.1 |
| AsPh$_3$ | 306.24 | 2.21 g | 7.22 | 0.1 |
| Cs$_2$CO$_3$ | 325.82 | 35.3 g | 108.3 | 1.5 |
| Anhydrous DMF | | 335 mL | | 10 vol. |

In the meantime, equip a 1-L, three-neck, RBF with a mechanical stirrer, a J-Kem temperature controller, and a nitrogen inlet.
Purge with nitrogen.
Charge the flask with 1 and DMF and degas the mixture.
Charge the flask with the catalyst, ligand, and cesium carbonate.
Cool the batch to about 18±5° C., but preferably at 18±2° C.
Add the solution prepared in Part 1 into the solution 1 while maintaining the temperature at about 23±3° C. rapidly over few minutes.
Allow the resulting brown solution agitate at 25±5° C.
Analyze by TLC (10% EtOAc/hexanes) after 2.5 h for complete reaction
Pour the reaction mixture onto ice-water (about 800 mL) with stirring.
Extract with EtOAc (about 3×330 mL).
Wash the combined organic with brine (about 200 mL).
Dry over sodium sulfate and concentrate to a dark brown oil (120 g).
Purify on silica gel eluting with 0-4% ethyl acetate/hexanes or heptanes.
Concentrate and dry under HIVAC at 25-30° C. for about 18-24 h.
Using the procedure described in Steps 4.1 and 4.2, Fragment A-B-C (2) was obtained as a colorless gum, 62.5 g (95% yield), >90% pure by HPLC and NMR, m/z 794.6 (M-TES). $^1$H NMR was consistent with the structure of the compound.

The third stage of the process was the removal of the protecting groups of Fragment A-B-C. The procedure is described in detail below.

Step 5.1

| Reagent | MW | Amount | mmol | Equiv. |
|---|---|---|---|---|
| Fragment A-B-C (2) | 908.59 | 61.29 g | 67.48 | 1 |
| 2,6-Lutidine | 107.16 | 78.2 mL | 674.8 | 10 |
| TMSOTf | 222.25 | 61 mL | 337.4 | 5 |
| DCM | | 915 mL | | 15 vol. |

Purge a 3-L, three-neck, RBF equipped with a mechanical stirrer, a J-Kem temperature controller, and a nitrogen inlet with nitrogen
Charge the flask with 2 and DCM.
Cool the reaction mixture to 0-5° C.
Add 2,6-lutidine dropwise at about −5-10° C. 0-5° C., but preferably at 0-5° C. over 5 min, followed by TMSOTf at the same temperature over 5 min.
Allow to stir at the same temperature for about 2-3 h.
Analyze the batch by TLC (10% EtOAc/hexanes) after about 2 h for complete reaction.
Quench with 0.5 N HCl (735 mL, 12 vol) added dropwise at about −5±10° C., but preferably at 5±5° C. over 65 min.
Separate the organic layer and extract the aqueous layer with DCM (about 2×100 mL).
Wash the combined organic with brine (200 mL).
Dry over sodium sulfate and concentrate to a colorless oil (72 g crude product).

Step 5.2

| Reagent | MW | Amount | mmol | Equiv. |
|---|---|---|---|---|
| Crude Acid (4) | 852.48 | 61 g | 67 | 1 |
| 0.2N HCl in MeOH | | 152 mL | — | 2.5 vol. |
| THF | | 152 mL | — | 2.5 vol. |

Dissolve the crude acid 4 in THF.
Cool the batch to about 0-5° C.
Add a 0.2 N solution of HCl in methanol at about 0±5° C., but preferably at 2±2° C. over 5 min.

Allow the mixture agitate at about 0±10° C., but preferably at 0±5° C. for 5-6 h.
Analyze by TLC (30% EtOAc/hexanes) for complete reaction.
Dilute the reaction mixture with ethyl acetate (about 450 mL).
Wash the mixture with brine (about 5×150 mL) until most residual HCl is removed.
Dry the solution over sodium sulfate and concentrate to a thick oil (64 g).
Purify on silica gel eluting with 10-50% ethyl acetate/hexanes or heptanes.
Concentrate and dry under HIVAC at 25-30° C. for about 24 h.

Using the procedure described in Steps 5.1 and 5.2, the hydorxyacid 5 was obtained as a white foam, 47.7 g (95% yield), 93.3% pure by HPLC, m/z 738.8. $^1$H NMR was consistent with the structure of the compound.

The fourth stage of the process is the macrolactonization of deprotected Fragment A-B-C. The procedure is described in detail below. Comparative yields of the product from the present invention and from the prior art processes are given in Table 2.

TABLE 2

Macrolactonization Reaction

| Laboratory | R1 | R2 | R3 | R4 | Yield (2 steps) | Ref |
|---|---|---|---|---|---|---|
| Present Invention | SiEt$_3$ | TBS | TBS | COO t-Bu | 95%, 87% (82.65%) | |
| Danishefsky et al. | SiEt$_3$ | SiEt$_3$ | Troc | COO t-Bu | 69%, 78% (53.82) | 11c22 |
| Danishefsky et al. | OH | SiEt$_3$ | Troc | COOH | 78% | 17 |
| Shibasaki et al. | H | TBS | TBS | COOPh | 84%, 88%, 99% (73) | 1424 |
| Liu et al. | OH | PMB | TBS | COOH | 40.5% | 18 |
| H C Wong et al. | Ac | TBS | PMB | COO t-Bu | 85%(Epo A) | 16 |
| White et al. | OH | TBS | TBS | COOH | 63% | 19 |
| Ermolenko et al. | TBS | TBS | TBS | COO t-Bu | 51% | 20 |
| E J Thomas et al. | SEN | TBS | H | COOH | 62%, 62% (38.44) | 21 |
| Avery et al. | SEM | TBS | Troc | COOH | 38% | 22 |
| Panek et al. | Ac | TBS | TBS | COOiPr | 62%, 73% (45.2) | 15 |

Step 6.1

| Reagent | MW | Amount | mmol | Equiv. |
|---|---|---|---|---|
| Deprotected A-B-C (5) | 738.22 | 45.12 g | 61.11 | 1 |
| Triethylamine | 101.19 | 51.1 mL | 366.68 | 6 |
| 2,4,6-Trichlorobenzoyl Chloride | 243.9 | 47.7 mL | 305.55 | 5 |
| Anhydrous THF | | 1.8 L | | 40 vol. |
| Anhydrous Toluene | | 2.48 L | — | 55 vol. |

Purge a 5-L, three-neck, RBF equipped with a mechanical stirrer, a J-Kem temperature controller, and a nitrogen inlet with nitrogen.
Charge the flask with a solution of Deprotected ABC in THF (1.8 L).
Cool the reaction mixture to about 0-5° C.
Add triethylamine at about 0-5° C. over about 2 min, followed by TMSOTf at the same temperature over 5 min.
Allow the solution stir at the same temperature for 1 h (Solution A).

Part 2

| Reagent | MW | Amount | mmol | Equiv. |
|---|---|---|---|---|
| DMAP | 122.17 | 74.6 g | 611.1 | 10 |
| Anhydrous Toluene | | 12.4 L | — | 275 vol. |

Purge a separate 22-L, three-neck reactor equipped with a mechanical stirrer, a J-Kem temperature controller, and a nitrogen inlet with nitrogen.
Charge the reactor with DMAP and toluene (12.4 L) at ambient temperature (15±25° C.), but preferably at about 22±2° C.
Stir the solution at the same temperature for 5 min (Solution B).
Dilute the Solution A prepared in Part 1 with toluene (2.48 L).
Add Solution A into Solution B with high agitation at about 15±25° C., but preferably at about 22±2° C. over about 6 h.
Use an extra 50 mL toluene to rinse the lines into Solution B.
Allow the resulting light white suspension to stir at the same temperature overnight.
Analyze by TLC (30% EtOAc/hexanes) for complete reaction.
Quench the reaction mixture with 0.5 N aqueous HCl solution (1.2 L) to pH 4-5 at about 15±25° C., but preferably at about 22±2° C. over 15 min.
Separate the organic layer and wash with brine (about 2×1 L).
Dry the solution over sodium sulfate and concentrate to a gum (83 g).
Purify on silica gel eluting with 0-5% ethyl acetate/hexanes.
Concentrate and dry under HIVAC at about 25-30° C. for about 24 h.

Using the procedure described in Steps 6.1 and 6.2, Protected Epo D (6) was obtained as a white foam, 40.0 g (86.8% yield), 99% pure by HPLC, m/z 720.8, 721.8. $^1$H NMR consistent with the structure.

The fifth stage of the process is the synthesis of Epothilone D (7). The procedure is described in detail below.
Step 7

| Reagent | MW | Amount | mmol | Equiv. |
|---|---|---|---|---|
| Protected Epo D (6) | 720.20 | 39.5 g | 54.84 | 1 |
| TFA | 114.02 | 316 mL | | 8 vol. |
| DCM | | 1.58 L | — | 40 vol. |

Purge a 12-L, three-neck, RBF equipped with a mechanical stirrer, a J-Kem temperature controller, and a nitrogen inlet with nitrogen.
Charge the flask with a solution of Protected Epo D in DCM under nitrogen.
Cool the reaction mixture to about −5-10° C., but preferably at 0-5° C.
Add TFA at about 0-5° C. over about 15 min.
Allow the solution stir at the same temperature for about 2 h.
Analyze by TLC (50% EtOAc/hexanes) for complete reaction.
Quench the reaction mixture with a saturated solution of bicarbonate (3 L) and solid sodium carbonate (120 g) in portion at about 0±10° C., but preferably at 5±5° C. over 45 min.

Separate the organic layer.
Extract the aqueous layer with DCM (about 500 mL).
Dry the combined organic solution over sodium sulfate and concentrate to a thick gum (~40 g).
Purify on silica gel eluting with 20-40% ethyl acetate/hexanes or heptanes.
Concentrate and dry under HIVAC at about 20-35° C., but preferably at 25-30° C. for about 24 h.

Using the procedure described in Step 7, Epo D (7) was obtained as a white foam, 24.62 g (91% yield), 93.4% pure by HPLC, m/z 492.5. $^1$H NMR consistent with the structure.

The sixth stage of the process is the synthesis of the key intermediate, Epo B, (which also a potent antitumor) in two steps. The procedure is described in detail below. Comparative yields of the product from the present invention and from the prior art processes are given in Table 3.

TABLE 3

Synthesis of Epo B.

| Laboratory | R2 | R3 | Reagent | Yield | Ref |
|---|---|---|---|---|---|
| Present Invention | H | H | m-CPBA | 60% | |
| White et al. | H | H | DMDO | 78% (Mixture of Isomers) | 19 |
| Avery et al. | H | H | m-CPBA | 30% | 13 |
| Avery et al. | H | H | DMDO | 53% (9.5/1) | 22 |
| Danishefsky et al. | H | H | DMDO | 70% (14/1) | 11c |
| Danishefsky et al. | H | H | DMDO | 49% | 11b |
| Nicolaou et al. | H | H | DMDO | 75% (5/1) | 23 |
| Panek et al. | H | H | CH$_3$C(NH)OOH | 60% | 15 |
| Altmann et al. | H | H | MeReO$_3$,H$_2$O$_2$ | 72% (9/1) | 24 |
| Shibasaki et al. | H | H | DMDO | 97% (Mixture of Isomers) | 14a |
| Lin et al. | H | H | m-CPBA | 83% (4/1) | 6 |
| Keck | H | H | DMDO | 82% (Mixture of Isomers) | 25 |

Step 8.1 (Oxidation)

| Reagent | MW | Amount | mmol | Equiv. |
|---|---|---|---|---|
| Epo D (7) | 491.68 | 24.3 g | 49.46 | 1 |
| m-CPBA (~75%) | 172.57 | 29.6 g + 22.8 g | | 2.6 + 2 |
| DCM | | 1.65 L | — | 68 vol. |

Purge a 3-L, three-neck, RBF equipped with a mechanical stirrer, a J-Kem temperature controller, and a nitrogen inlet with nitrogen.
Charge the flask with a solution of Epo D in DCM.
Cool the reaction mixture to less than −25° C.
Add m-CPBA (2.6 equiv) in one portion.
Allow the mixture vigorously stir at about −30±15° C., but preferably at −25±5° C. for about 1.5 h.
Add an additional 2 equivalent m-CPBA at about −20° C. in one portion.
Allow the mixture vigorously stir at about −25±5° C. for 3.5 h.
Analyze the batch by TLC (40% EtOAc/hexanes) for complete reaction.
Step 8.2 (Work Up)
Equip a 12-L, three-neck, reactor with a mechanical stirrer, a J-Kem temperature controller, and a vacuum line.
Charge the reactor with a saturated solution of bicarbonate (2 L) and a 20% aqueous solution of sodium sulfite (0.8 L).
Transfer the batch into to the above solution at about 20±5° C., but preferably at 22±2° C.
Vigorously stir for 30 min until the off-gassing is ceased, and the starch-potassium iodide paper confirms presence of no peroxide.
Separate the organic layer.
Extract the aqueous layer with DCM (about 2×500 mL).
Wash the combined organic solution with brine (about 500 mL).
Dry the organic solution over sodium sulfate and concentrate to a white foam (26.1 g).
Purify on silica gel eluting with 20-40% ethyl acetate/hexanes or heptanes.
Concentrate the fractions containing the product and the undesired diastereomer, 3.5:1 ratio, respectively to a white foam.
Dissolve the mixture in DCM (about 100 mL) and dilute with ethyl acetate (about 50 mL).
Remove DCM by rotovap at about 15-25° C., but preferably at 20-25° C. (solvent swap with ethyl acetate).
Allow crystallization at about 20±5° C., but preferably at 22±2° C. for 1 h.
Filter the crystals and wash with 1:1 ethyl acetate/hexanes (2×25 mL).
Dry the crystals under HIVAC at about 20-30° C. for about 24 h.

Using the procedure described in Steps 8.1 and 8.2, Epo B (Fomula IV) was obtained as white crystals, 10.4 g (41.4% yield), 1$^{st}$ Crop, 99.53% pure by HPLC (contained 0.47% of the major wrong diastereomer), m/z 508.5 (M+1). $^1$H NMR consistent with the structure.
Step 8.3. Crystallization of the Filtrate, 2$^{nd}$ Crop:
Concentrate the filtrate to a white solid.
Dissolve the solid in DCM (about 50 mL) and dilute with ethyl acetate (about 25 mL).
Remove DCM by rotovap at about 20-25° C. (solvent swap with ethyl acetate).
Dilute the ethyl acetate solution with hexanes (25 mL).
Allow crystallization at about 20±5° C., but preferably at 22±2° C. for 24 h.
Filter the crystals and wash with 1:1 ethyl acetate/hexanes (about 2×25 mL).
Dry the crystals under HIVAC at about 20-30° C. for 24 h.
Using the procedure described in Step 8.3, Epo B (Formula IV) was obtained as white crystals, 3.8 g (15% yield), 2$^{nd}$ Crop, 98.4% pure by HPLC (contained 1.4% of the undesired diastereomer), m/z 508.5 (M+1).
Step 8.4. Crystallization of the Filtrate, 3rd Crop:
Concentrate the filtrate to an oil (~11 g).
Dilute with 2:1 ethyl acetate/hexanes (about 30 mL).
Allow crystallization at about 20±5° C., but preferably at 22±2° C. 3 h.
Filter the crystals and wash with 1:2 ethyl acetate/hexanes (about 2×15 mL) and hexanes (15 mL).
Dry the crystals under HIVAC at 20-30° C. for 24 h.
Using the procedure described in Step 8.4, Epo B (Formula IV) was obtained as white crystals, 0.48 g (1.9% yield), 3$^{rd}$ Crop, 97.2% pure by HPLC (contained 2.4% of the undesired diastereomer), m/z 508.5 (M+1).
Step 8.5. Crystallization of the Filtrate, 4$^{th}$ Crop
Concentrate the filtrate to an oil (~10 g, 15.7% product and 78.2% of the undesired diastereomer by HPLC).
Dilute with 4:1 ethyl acetate/hexanes (about 25 mL).
Seeds the solution with pure Epo B crystals (about 5 mg).
Allow crystallization at about 20±5° C., but preferably at 22±2° C. 24 h.
Filter the crystals and wash with 1:4 ethyl acetate/hexanes (about 2×25 mL).
Dry the crystals under HIVAC at about 20-30° C. for 24 h.

Using the procedure described in Step 8.5, Epo B (Formula IV) was obtained as white crystals, 0.508 g (2% yield), 4$^{th}$ Crop, 96.1% pure by HPLC (contained 3.3% of the undesired diastereomer), m/z 508.5 (M+1).

Step 8.6. Re-Crystallization of the 3$^{rd}$ Crop from Ethyl Acetate/Hexanes

Dissolve the solid (0.48 g, 97.2% pure) in DCM (about 5 mL) and dilute with ethyl acetate (about 5 mL).
Remove DCM by rotovap at about 20-25° C. (solvent swap with ethyl acetate).
Dilute the ethyl acetate solution with hexanes (about 10 mL).
Allow crystallization at about 20±5° C., but preferably at 22±2° C. 24 h.
Filter the crystals and wash with 1:5 ethyl acetate/hexanes (about 2×6 mL) and hexanes (about 6 mL).
Dry the crystals under HIVAC at about 20-30° C. for about 24 h.
Using the procedure described in Step 8.6, Epo B (Formula IV) was obtained as white needles, 0.303 g (63%), 99.61% pure by HPLC (contained 0.23% of the major wrong diastereomer), m/z 508.5 (M+1).

Step 8.7. Re-Crystallization of the 4$^{th}$ Crop from Acetone/Hexanes

Dissolve the solid (0.505 g, 96.1% pure) in acetone (about 10 mL) at about 35-40° C.
Dilute with hexanes (about 20 mL).
Allow crystallization with a tight cap at about 20±5° C., but preferably at 22±2° C. 24 h.
Filter the crystals and wash with 4:1 hexanes/acetone (about 25 mL). Dry the crystals under HIVAC at about 20-30° C. for about 24 h.
Using the procedure described in Step 8.7, Epo B (Formula IV) was obtained as white needles, 0.237 g (54%), 99.76% pure by HPLC (contained 0.08% of the undesired diastereomer), m/z 508.5 (M+1). Crystallization of the above filtrate with a loose cap resulted in isolation of 99 mg (20%) more crystals with a purity of 99.61%.

Synthesis of Ixabepilone—The process of conversion of Epo B to the desired Ixa in this invention is distinct from the steps that were previously published[7,26] in the following ways:
a) it eliminates the catalytic hydrogenation or the use of phosphine-based reduction for the reduction of the intermediate azide, and b) takes advantage of TBTU as a coupling agent for macrolactamization. No intermediates are required to be purified in this invention and the final API is crystallized from Acetone-hexanes in overall 23% yield and purity >98%.

The seventh stage: synthesis of the azidoacid intermediate 8. The procedure is described in detail below.

Step 9.1

| Reagent | MW | Amount | mmol | Equiv. |
| --- | --- | --- | --- | --- |
| Epo B (Formula IV) | 507.68 | 5.00 g | 9.848 | 1 |
| Sodium Azide | 65.01 | 0.800 | 12.311 | 1.25 |
| Pd(PPh$_3$)$_4$ | 1155.58 | 0.569 g | 0.492 | 0.05 |
| THF/Water | | 100 mL | — | 20 vol. |

Purge a 500-mL, three-neck, RBF equipped with a mechanical stirrer, a J-Kem temperature controller, and a nitrogen inlet with nitrogen.
Charge the flask with THF (about 90 mL) and DI water (about 10 mL).
Degas the solvent with stirring three times.
Charge the batch with Epo B and sodium azide under nitrogen with stirring.
Degas the mixture once more.
Add the catalyst under nitrogen with stirring.
Warm the resulting turbid solution to about 40±10° C., but preferably at 42±2° C. over about 10 min.
Stir the batch at the same temperature for about 20 min.
Analyze the clear light yellow solution by TLC (EtOAc) or LCMS for complete reaction.

Step 9.2 (Work Up)

Cool the reaction mixture to below 30° C.
Dilute the mixture with hexanes (about 300 mL, 60 vol.) with stirring.
Stir vigorously for about 5 min.
Allow phase separation for at least 10 min.
Separate the aqueous layer (the batch) and extract the organic layer with DI water (about 7.5 mL, 1.5 vol).
Allow phase separation for at least 10 min.
Separate the aqueous layer, and extract the organic layer again with DI water (about 7.5 mL).
Allow phase separation for at least 10 min.
Separate the aqueous layer.
Analyze the aqueous solution (the batch, ~25 mL) by HPLC (a typical process should give 80-85% of the azide and 12-15% of one major byproduct (undesired diastereomer).
Dilute the azide solution with absolute ethanol (about 75 mL).
Degas the resulting 3:1 ethanol/water solution twice.
Progress the azide solution (8) to the next step for reduction to the amine.

The eighth stage of the process is the synthesis of the amino acid. The procedure is described in detail below.

Step 10.1

| Reagent | MW | Amount | mmol | Equiv. |
| --- | --- | --- | --- | --- |
| Azidoacid (8) Solution | 550.71 | ~5 g Crude Mixture | ~9.8 | 1 |
| Zinc Dust | 65.37 | 1.93 g | 29.5 | 3 |
| Ammonium Chloride | 53.5 | 1.89 g | 35.4 | 3.6 |
| Ethanol/Water | | 100 mL | — | 20 vol. |

Purge a 500-mL, three-neck, RBF equipped with a mechanical stirrer, a J-Kem temperature controller, and a nitrogen inlet with nitrogen.
Charged the flask with the degassed solution of the azide prepared in the previous step (about 100 mL).
Charge the flask with ammonium chloride, followed by zinc dust at about 20±5° C., but preferably at 22±2° C. with stirring under nitrogen.
Allow stirring for about 3 h.
Analyze the batch by LCMS for complete reaction.

Step 10.2 (Work Up)

Filter the reaction mixture and wash the cake with ethanol (about 2×15 mL).
Concentrate the filtrate to dryness at about 25-30° C. under HIVAC.
Dissolve the crude mixture in 5% MeOH/DCM (about 50 mL) and stir for 5 min to precipitate the ammonium salts.
Filter and wash the cake with 5% MeOH/DCM (about 2×25 mL).
Concentrate the filtrate to a beige solid (5.3 g) at about 25-30° C. under HIVAC.
Re-dissolve the crude solid in 5% MeOH/DCM (about 25 mL) and dilute the solution with ethyl acetate (about 25 mL).

Concentrate the solution to about 15 mL (solvent swap with EtOAc) at about 25-30° C. under HIVAC.

Dilute the ethyl acetate solution with hexanes or heptanes (about 15 mL).

Allow the mixture to stand for 5 min for full trituration of the product as a sticky solid.

Remove the solution containing impurities.

Dry the crude product 9 to a constant weight at 25-30° C. under HIVAC for about 24 h.

Analyze the resulting crude beige solid (5.25 g, quantitative) by HPLC (a typical process should give 75-80% of the amino acid 9 and 15-20% of the undesired diastereomer.

Progress the crude solid to the next stage for the macrolactamization to ixabepilone.

The final stage of the process is the synthesis of the desired final product, the API, Ixabepilone. The procedure is described in detail below.

Step 11.1

| Reagent | MW | Amount | mmol | Equiv. |
|---|---|---|---|---|
| Amino Acid (9) | 524.71 | 5.25 g Crude Mixture | ~10 | 1 |
| TBTU | 321.11 | 4.34 g | 13.5 | 1.35 |
| Sodium Bicarbonate | 84.01 | 1.14 g | 13.5 | 1.35 |
| Acetone (dry) | — | 210 mL | — | 40 vol. |
| NMP (anhydrous) | — | 52.5 mL | — | 10 vol |

Purge a 500-mL, three-neck, RBF equipped with a mechanical stirrer, a J-Kem temperature controller, and a nitrogen inlet with nitrogen.

Charged the flask with the amino acid and sodium bicarbonate, followed by acetone with stirring.

Cool the batch to about 0-5° C.

Charge the batch with TBTU in one portion, followed by NMP at about 0-5° C. over about 5 min.

Allow the reaction stir at about 0-5° C. and monitor by HPLC.

Analyze the batch by HPLC for complete reaction after 3 h.

Step 11.2 (Work Up)

Quench the batch with DI water (0.5 mL, 0.1 vol) at 0-5° C.

Concentrate the reaction mixture at about 15-30° C., but preferably at 20-25° C. by rotovap to remove acetone.

Cool the NMP solution to about 0-5° C.

Charge the batch with crushed ice (50 g), followed by ice-water (about 150 mL) at 0-5° C.

Extract the batch with ethyl acetate (about 6×50 mL, Note: allow phase separation between each extraction for at least 5 min).

Wash the combined organic solution with brine (about 50 mL).

Dry the organic solution over $Na_2SO_4$.

Filter and wash with ethyl acetate (about 50 mL).

Concentrate the filtrate to a yellow oil containing residual NMP.

Analyze the crude oil (8.3 g) by HPLC (a typical process should show 60-65% of the product (Formula III) and 10-15% each of two major byproducts (undesired diastereomers).

Step 11.3 (Purification)

Pack a silica gel plug with pre-quenched silica gel (about 250 ml, 50 vol) and DCM (Note: a stocked pre-quenched silica gel was prepared by making a slurry of silica gel in 10:1:0.1 DCM/MeOH/$NH_4OH$, filtering, and drying in air for at least 48 h prior to use).

Dilute the crude oil with 1:1 DCM/hexanes (about 20 mL) and load onto the silica gel.

Elute with 0-2% MeOH/DCM.

Pool the pure fractions and concentrate to a white solid.

Dry under HIVAC at about 25-30° C. for 24 h.

Using the procedure described in Steps 11.1 to 11.3, the final product ixabepilone (Epothilone of Formula III) was obtained as a white solid, 1.15 g (23% for 3 steps), 98.57% pure by HPLC. Mixed Fractions: Ixabepilone+the Major Byproduct (3:1), yellow solid, 0.189 g, (4% for 3 steps), 71.0% pure by HPLC.

Step 11.4 (Crystallization)

Dissolve the solid in DCM (15 mL) and dilute the solution with acetone (about 15 mL).

Concentrate the solution by rotovap to about 10 mL at about 15-30° C., but preferably at 20-25° C. (solvent swap with acetone).

Dilute the acetone solution with hexanes or heptanes (about 10 mL).

Allow crystallization at about 20±5° C., but preferably at 22±2° C. for 24 h.

Filter the crystals and wash with 4:1 hexanes/acetone (about 2×10 mL).

Dry the crystals under HIVAC at 25-30° C. for 24 h.

Using the procedure described in Steps 11.1 to 11.3, the final product ixabepilone was obtained as white crystals, 918 mg (19%), 99.62% pure by HPLC. $^1H$ NMR is consistent with the structure.

The present invention discloses the least arduous, most practical, scalable, process for the manufacture of Ixabepilone. The manufacturing process of the present invention involves two synthetic steps less than the previously reported in the literature (9 vs. 11). Further advantages of the present invention are summarized below.

1. The invention describes total synthetic Epothilone B that lacks the impurities such as Epo A, Epo C, Epo D and C21-hydroxy derivatives that have been observed in the fermentation route to Epothilone B. The major impurity (>0.1%) that has been isolated and identified is the sole stereoisomer at the epoxide (C12-C13) position.
2. Total recovery of crystallized Epo B from crude synthetic mixture in this invention is remarkably high (61%, purity>98.7%).
3. The favorable yield and the purity of the synthetic Epo B provides scalability advantage over the fermentation process.
4. Extensive screening resulted in identifying a derivative of fragment B that produces major enhancement, both in the preparation of the Z-vinyl iodide intermediate (55.8% from reported 43%) and the key B-alkyl Suzuki coupling with the fragment A-C (95% coupling, single isomer).
5. The B-alkyl Suzuki coupling route disclosed in the present invention is a plant-level efficient and accessible approach to the smooth production of large quantities of Epo B.
6. The manufacturing process of current invention has increased the total yield of Ixabepilone from Epothilone by 25%? (18% vs. 23%).
7. The invention discloses purification and crystallization process for the oxidation step of Epo D to Epo B that gives rise to an unanticipated, remarkable recovery of 54%.

REFERENCES

1. Fletcher, J. H.; Dermer, O. C.; Fox, R. B.; Nomenclature, A. C. S. C. o., *Nomenclature of organic compounds: principles and practice*. American Chemical Society: 1974.

2. Hellwinkel, D., *Systematic Nomenclature of Organic Chemistry: A Directory to Comprehension and Application on Its Basic Principles; with 35 Tables*. Springer Berlin Heidelberg: 2001.
3. Tang, L.; Shah, S.; Chung, L.; Carney, J.; Katz, L.; Khosla, C.; Julien, B., Cloning and heterologous expression of the epothilone gene cluster. *Science* 2000, 287 (5453), 640-2.
4. Mulzer, J.; Altmann, K.-H.; Höfle, G.; Müller, R.; Prantz, K., Epothilones—A fascinating family of microtubule stabilizing antitumor agents. *Comptes Rendus Chimie* 2008, 11 (11-12), 1336-1368.
5. Chappell, M. D.; Stachel, S. J.; Lee, C. B.; Danishefsky, S. J., En Route to a Plant Scale Synthesis of the Promising Antitumor Agent 12,13-Desoxyepothilone B. *Organic Letters* 2000, 2 (11), 1633-1636.
6. Wang, J.; Sun, B.-F.; Cui, K.; Lin, G.-Q., An Efficient Total Synthesis of (−)-Epothilone B. *Organic Letters* 2012, 14 (24), 6354-6357.
7. Kim, S. H.; Borzilleri, R. M., Process for the preparation of ring-opened epothilone intermediates which are useful for the preparation of epothilone analogs. Google Patents: 2002.
8. Hofle, G., The epothilones: an outstanding family of anti-tumor agents. General aspects. *Fortschr Chem Org Naturst* 2009, 90, 5-28.
9. Nicolaou, K. C.; Sarabia, F.; Ninkovic, S.; Yang, Z., Total Synthesis of Epothilone A: The Macrolactonization Approach. *Angewandte Chemie International Edition in English* 1997, 36 (5), 525-527.
10. Rivkin, A.; Cho, Y. S.; Gabarda, A. E.; Yoshimura, F.; Danishefsky, S. J., Application of Ring-Closing Metathesis Reactions in the Synthesis of Epothilones⊥. *Journal of Natural Products* 2004, 67 (2), 139-143.
11. (a) Balog, A.; Meng, D.; Kamenecka, T.; Bertinato, P.; Su, D.-S.; Sorensen, E. J.; Danishefsky, S. J., Total Synthesis of (−)-Epothilone A. *Angewandte Chemie International Edition in English* 1996, 35 (23-24), 2801-2803; (b) Su, D.-S.; Meng, D.; Bertinato, P.; Balog, A.; Sorensen, E. J.; Danishefsky, S. J.; Zheng, Y.-H.; Chou, T.-C.; He, L.; Horwitz, S. B., Total Synthesis of (−)-Epothilone B: An Extension of the Suzuki Coupling Method and Insights into Structure-Activity Relationships of the Epothilones. *Angewandte Chemie International Edition in English* 1997, 36 (7), 757-759; (c) Harris, C. R.; Kuduk, S. D.; Balog, A.; Savin, K.; Glunz, P. W.; Danishefsky, S. J., New Chemical Synthesis of the Promising Cancer Chemotherapeutic Agent 12,13-Desoxyepothilone B: Discovery of a Surprising Long-Range Effect on the Diastereoselectivity of an Aldol Condensation. *Journal of the American Chemical Society* 1999, 121 (30), 7050-7062; (d) Harris, C. R.; Kuduk, S. D.; Danishejky, S. J., Chemical Synthesis and Biological Studies of the Epothilones—Microtubule Stabilizing Agents with Enhanced Activity Against Multidrug-Resistant Cell Lines and Tumors. In *Chemistry for the 21st Century*, Wiley-VCH Verlag GmbH: 2007; pp 8-36.
12. Broadrup, R. L.; Sundar, H. M.; Swindell, C. S., Total synthesis of 12,13-desoxyepothilone B (Epothilone D). *Bioorganic Chemistry* 2005, 33 (2), 116-133.
13. Watkins, E. B.; Chittiboyina, A. G.; Avery, M. A., Recent Developments in the Syntheses of the Epothilones and Related Analogues. *European Journal of Organic Chemistry* 2006, 2006 (18), 4071-4084.
14. (a) Sawada, D.; Kanai, M.; Shibasaki, M., Enantioselective Total Synthesis of Epothilones A and B Using Multifunctional Asymmetric Catalysis. *Journal of the American Chemical Society* 2000, 122 (43), 10521-10532; (b) Sawada, D.; Shibasaki, M., Enantioselective Total Synthesis of Epothilone A Using Multifunctional Asymmetric Catalyses. *Angewandte Chemie International Edition* 2000, 39 (1), 209-213.
15. Zhu, B.; Panek, J. S., Total Synthesis of Epothilone A. *Organic Letters* 2000, 2 (17), 2575-2578.
16. Liu, J.; Wong, C.-H., Aldolase-Catalyzed Asymmetric Synthesis of Novel Pyranose Synthons as a New Entry to Heterocycles and Epothilones. *Angewandte Chemie International Edition* 2002, 41 (8), 1404-1407.
17. Balog, A.; Harris, C.; Savin, K.; Zhang, X.-G.; Chou, T.-C.; Danishefsky, S. J., A Novel Aldol Condensation with 2-Methyl-4-pentenal and Its Application to an Improved Total Synthesis of Epothilone B. *Angewandte Chemie International Edition* 1998, 37(19), 2675-2678.
18. Liu, Z.-Y.; Chen, Z.-C.; Yu, C.-Z.; Wang, R.-F.; Zhang, R.-Z.; Huang, C.-S.; Yan, Z.; Cao, D.-R.; Sun, J.-B.; Li, G., Total Synthesis of Epothilone A through Stereospecific Epoxidation of the p-Methoxybenzyl Ether of Epothilone C. *Chemistry—A European Journal* 2002, 8 (16), 3747-3756.
19. White, J. D.; Carter, R. G.; Sundermann, K. F.; Wartmann, M., Total Synthesis of Epothilone B, Epothilone D, and cis- and trans-9,10-Dehydroepothilone D. *Journal of the American Chemical Society* 2001, 123 (23), 5407-5413.
20. Ermolenko, M. S.; Potier, P., Synthesis of epothilones B and D from d-glucose. *Tetrahedron Letters* 2002, 43 (16), 2895-2898.
21. Martin, N.; Thomas, E. J., Total syntheses of epothilones B and D: applications of allylstannanes in organic synthesis. *Tetrahedron Letters* 2001, 42 (47), 8373-8377.
22. Jung, J.-C.; Kache, R.; Vines, K. K.; Zheng, Y.-S.; Bijoy, P.; Valluri, M.; Avery, M. A., Total Syntheses of Epothilones B and D. *The Journal of Organic Chemistry* 2004, 69 (26), 9269-9284.
23. Nicolaou, K. C.; He, Y.; Vourloumis, D.; Vallberg, H.; Roschangar, F.; Sarabia, F.; Ninkovic, S.; Yang, Z.; Trujillo, J. I., The Olefin Metathesis Approach to Epothilone A and Its Analogues. *Journal of the American Chemical Society* 1997, 119 (34), 7960-7973.
24. Cachoux, F.; Isarno, T.; Wartmann, M.; Altmann, K.-H., Scaffolds for Microtubule Inhibition through Extensive Modification of the Epothilone Template. *Angewandte Chemie International Edition* 2005, 44 (45), 7469-7473.
25. Keck, G. E.; Giles, R. L.; Cee, V. J.; Wager, C. A.; Yu, T.; Kraft, M. B., Total Synthesis of Epothilones B and D: Stannane Equivalents for β-Keto Ester Dianions. *The Journal of Organic Chemistry* 2008, 73 (24), 9675-9691.
26. (a) Borzilleri, R. M.; Zheng, X.; Schmidt, R. J.; Johnson, J. A.; Kim, S.-H.; DiMarco, J. D.; Fairchild, C. R.; Gougoutas, J. Z.; Lee, F. Y. F.; Long, B. H.; Vite, G. D., A Novel Application of a Pd(0)-Catalyzed Nucleophilic Substitution Reaction to the Regio- and Stereoselective Synthesis of Lactam Analogues of the Epothilone Natural Products. *Journal of the American Chemical Society* 2000, 122 (37), 8890-8897; (b) Stachel, S. J.; Biswas, K.; Danishefsky, S. J., The Epothilones, Eleutherobins, and Related Types of Molecules. *Current Pharmaceutical Design* 2001, 7(13), 1277-1290; (c) Stachel, S. J.; Lee, C. B.; Spassova, M.; Chappell, M. D.; Bornmann, W. G.; Danishefsky, S. J.; Chou, T.-C.; Guan, Y., On the Interactivity of Complex Synthesis and Tumor Pharmacology in the Drug Discovery Process: Total Synthesis and Comparative in Vivo Evaluations of the 15-Aza Epothilones. *The Journal of Organic Chemistry* 2001, 66 (12), 4369-4378.

What is claimed is:

1. A process for the preparation of an epothilone compound represented by the formula

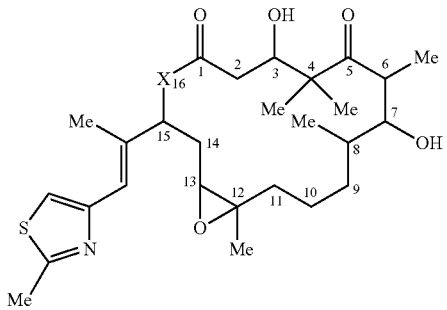

5 wherein X is NH or O;
the process comprising:
(a) preparing Fragment B represented by the formula

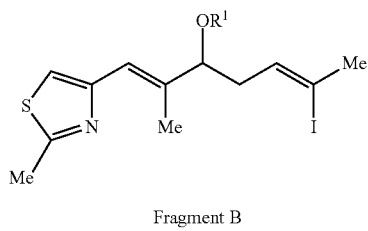

Fragment B wherein R¹ is a protecting group;
(b) coupling Fragment B with Fragment A-C

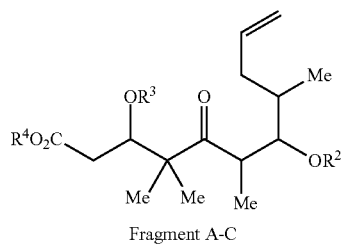

3

Fragment A-C to form Fragment A-B-C

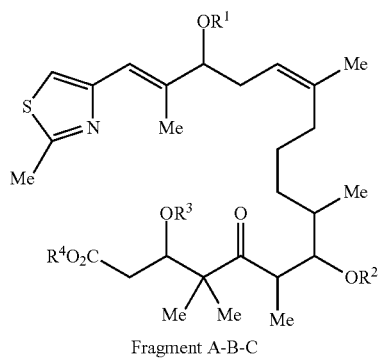

2

Fragment A-B-C wherein R², R³ and R⁴ are protecting groups;

(c) selectively removing the protecting group R⁴ from Fragment A-B-C to form carboxylic acid represented by structure 4

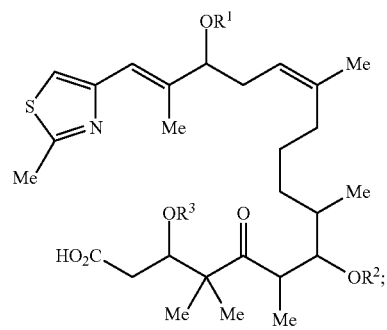

4

(d) selectively removing the protecting group R¹ from the carboxylic acid represented by structure 4 to form the hydroxyacid represented by structure 5

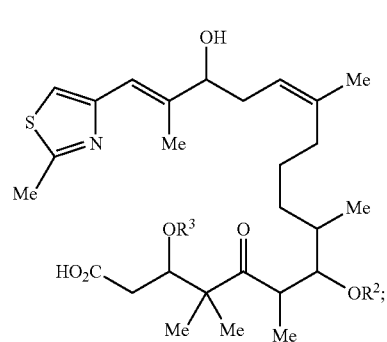

5

(e) macrocyclizing the hydroxyacid represented by structure 5 to form the lactone represented by structure 6

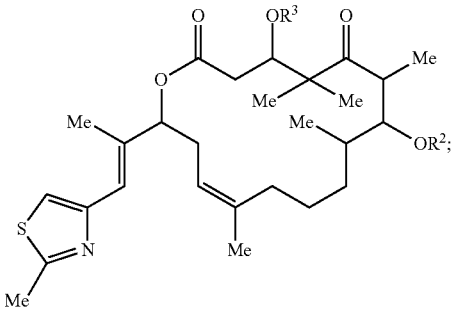

6

(f) removing the protecting groups R² and R³ from lactone 6 to form the epothilone represented by structure 7

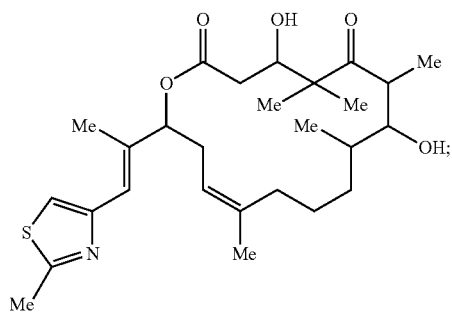

(g) selectively epoxidizing diol 7 at the C12-C13 double bond to form an epothilone compound represented by the structure;

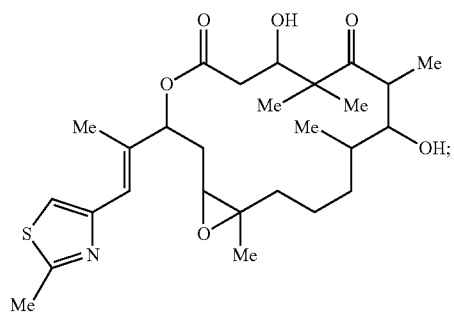 [SMILES: C/C(=C\c1csc(C)n1)C1CC2OC2(C)CCCC(C)C(O)C(C)C(=O)C(C)(C)C(O)CC(=O)O1]

(h) purifying the epothilone compound formed in step (g);
(i) reacting the purified product of step (g) with sodium azide in the presence of palladium tetrakistriphenylphosphine as catalyst to form an azidoacid represented by structure 8

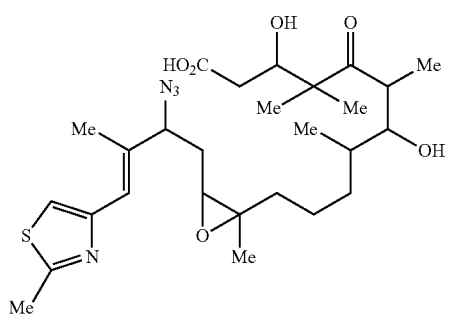

(j) selectively reducing the azide group of the azidoacid 8 to form an aminoacid represented by structure 9

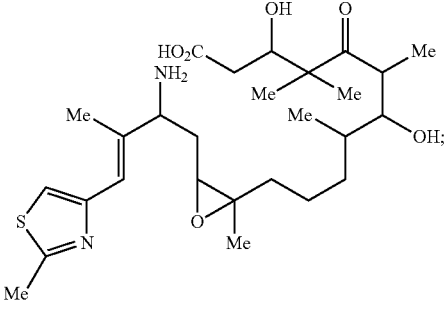

(k) cyclizing aminoacid 9 to form the compound of the formula;

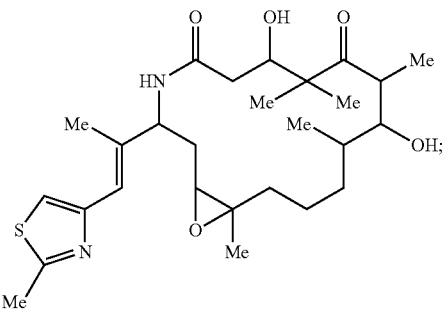 [SMILES: C/C(=C\c1csc(C)n1)C1CC2OC2(C)CCCC(C)C(O)C(C)C(=O)C(C)(C)C(O)CC(=O)N1]

and
(l) purifying the product of step (k).

2. The process of claim 1, wherein Fragment B is prepared a process comprising
(a) reacting a compound represented structure 10

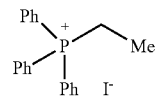

with n-BuLi and iodine to form a compound represented by structure 11

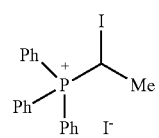

(b) isolating the product of step (a);
(c) reacting the isolated product of step (b) with a base to form a compound represented by structure 12

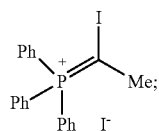

and
(d) reacting the compound represented by structure 12 with an aldehyde of formula

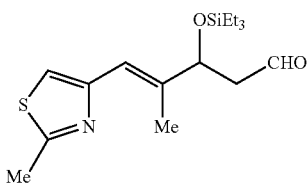

to form Fragment B, wherein $R^1$ in Fragment B is SiEt$_3$.

3. The process of claim 2, wherein the base employed in step (c) is sodium hexamethyldisilazide.

4. The process of claim 1, wherein Fragment B is prepared by a process comprising
(a) reacting a compound represented structure 10

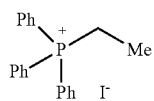

with n-BuLi and iodine to form a compound represented by structure 11

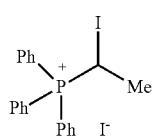

(b) reacting the compound of formula 11 with a base to for a compound represented by structure 12

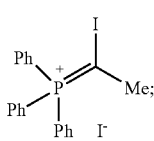

and
(c) reacting the compound represented by structure 12 with an aldehyde of formula

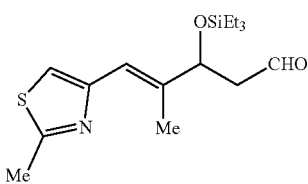

to form Fragment B.

5. The process of claim 4, wherein the base employed in step (b) is sodium hexamethyldisilazide.

6. The process of claim 1, wherein in step (c) the $R^4$ protecting group is deprotected with trimethysilyltriflate.

7. The process of claim 1, wherein in step (d) the triethylsilyl group is deprotected with dilute hydrochloric acid in methanol.

8. The process of claim 1, wherein in step (e) the hydroxyacid 5 is cyclized with 2,4,6-trichlorobenzoyl chloride.

9. The process of claim 1, wherein in step (f) protecting groups $R^2$ and $R^3$ are deprotected with trifluoroacetic acid.

10. The process of claim 1, wherein in step (g) diol 7 is epoxidized using 3-chloro-peroxybenzoic acid.

11. The process of claim 1, wherein in step (h) the epothilone compound is purified by recrystallization from dichloromethane/ethyl acetate/hexanes.

12. The process of claim 1, wherein in step (j) azoacid 8 is reduced using a reducing agent comprising zinc and ammonium chloride.

13. The process of claim 1, wherein in step (k) aminoacid 9 is cyclized using TBTU (O-(Benzotriazol-1-yl)-N,N,N', N'-tetramethyluronium tetrafluoroborate).

14. The process of claim 1, wherein in step (l) the product of step (k) is purified by recrystallization from acetone/hexanes or acetone/heptanes.

15. The process of claim 1, wherein the absolute configuration of the carbon atom bearing —OR$^1$ at position 15 in Fragment B is "S".

16. The process of claim 1, wherein the absolute configurations at positions 3, 6, 7, 8, and 15 in structure 4 are "S," "R", "S," "S," and "S" respectively.

17. The process of claim 1, wherein the absolute configurations at positions 3, 6, 7, 8, and 15 in structure 5 are "S," "R", "S," "S," and "S" respectively.

18. The process of claim 1, wherein the absolute configurations at positions 3, 6, 7, 8, and 15 in structure 6 are "S," "R", "S," "S," and "S" respectively.

19. The process of claim 1, wherein the absolute configurations at positions 3, 6, 7, 8, and 15 in structure 7 are "S," "R", "S," "S," and "S" respectively.

20. The process of claim 1, wherein the absolute configurations at positions 3, 6, 7, 8, 12, 13, and 15 in the epothilone compound prepared in step (g) are "S," "R", "S," "S," "R," "S," and "S" respectively.

21. The process of claim 1, wherein the absolute configurations at positions 3, 6, 7, 8, 12, 13, and 15 in structure 8 are "S," "R", "S," "S," "R," "S," and "S" respectively.

22. The process of claim 1, wherein the absolute configurations at positions 3, 6, 7, 8, 12, 13, and 15 in structure 9 are "S," "R", "S," "S," "R," "S," and "S" respectively.

23. The process of claim 1, wherein the absolute configurations at positions 3, 6, 7, 8, 12, 13, and 15 in the compound formed in step (k) are "S," "R", "S," "S," "R," "S," and "S" respectively.

24. A process for preparing ixabepilone comprising:
(a) one or more steps selected from
(i) reacting a compound of formula 1

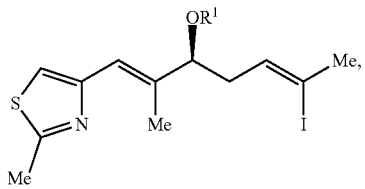

where R¹ is a protecting group, with Fragment A-C

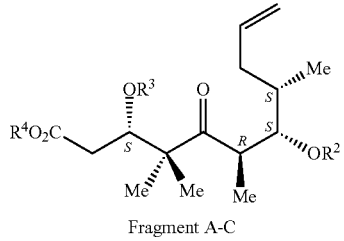

Fragment A-C to form Fragment A-B-C

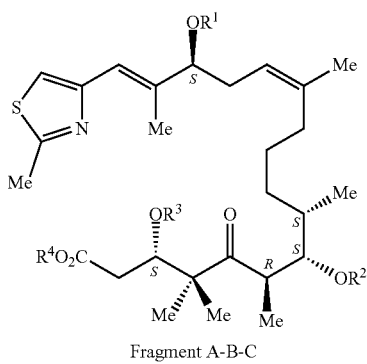

Fragment A-B-C where R², R³ and R⁴ are protecting groups;
(ii) selectively removing the R⁴ protecting group from Fragment A-B-C to give the compound of formula 4

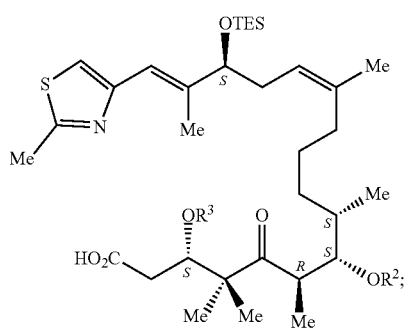

(iii) selectively removing the R¹ protecting group from the compound of formula 5 to give the hydroxy acid of formula 5

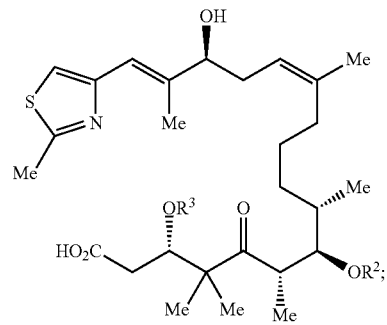

(iv) macrocyclizing the hydroxy acid of formula 5 to give the lactone of formula 6

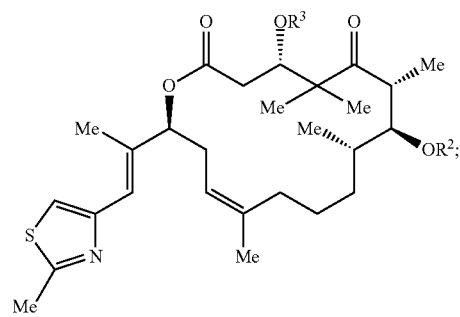

(v) deprotecting the lactone of formula 6 to form the diol of formula 7

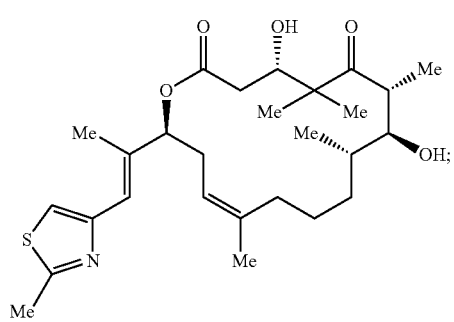

(vi) selectively epoxidizing the diol compound of formula 7 to form a compound of formula II Formula II

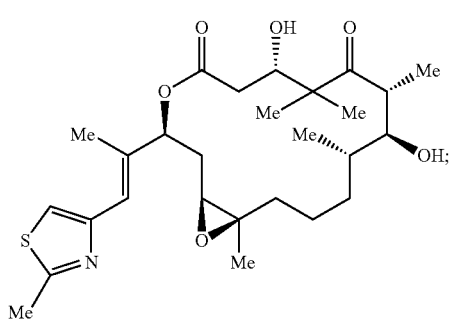

(vii) converting the compound of formula II to the azido acid of formula 8

8

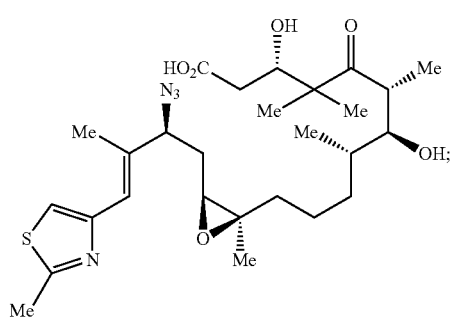

and
(viii) selectively reducing the azide group of the azido acid of formula 8 to give the amino acid of formula 9

9

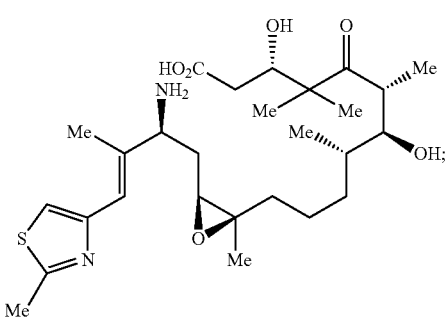

and
(b) converting the product of step (a) to ixabepilone.

25. The process of claim 24, wherein step (b) comprises cyclizing the amino acid of formula 9 to form ixabepilone.

26. The process of claim 10, wherein 4-6 molar equivalents of 3-chloro-peroxybenzoic acid is added in multiple portions.

27. The process of claim 24, wherein step (ix) comprises reacting the epothilone compound of formula II with an azide, optionally in the presence of a catalyst.

28. The method of claim 27, wherein the azide is sodium azide and the catalyst is palladium tetrakistriphenylphosphine.

29. The process of claim 1, wherein $R^2$ and $R^3$ are t-butyldimethylsilyl protecting groups and $R^4$ is a t-butyl protecting group.

30. The process of claim 24, wherein $R^2$ and $R^3$ are t-butyldimethylsilyl protecting groups and $R^4$ is a t-butyl protecting group.

* * * * *